US008076099B2

(12) United States Patent
Chambers et al.

(10) Patent No.: US 8,076,099 B2
(45) Date of Patent: Dec. 13, 2011

(54) **BIOMARKERS OF *FRANCISELLA* INFECTION**

(75) Inventors: James Chambers, San Antonio, TX (US); Jieh-Juen Yu, San Antonio, TX (US); Karl E. Klose, San Antonio, TX (US); M. Neal Guentzel, San Antonio, TX (US); Bernard P. Arulanandam, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 630 days.

(21) Appl. No.: 12/133,963

(22) Filed: Jun. 5, 2008

(65) Prior Publication Data

US 2008/0317742 A1    Dec. 25, 2008

Related U.S. Application Data

(60) Provisional application No. 60/942,027, filed on Jun. 5, 2007.

(51) Int. Cl.
*C12Q 1/02* (2006.01)
*C12Q 1/37* (2006.01)

(52) U.S. Cl. ............................................. 435/34; 435/23
(58) Field of Classification Search ........................ None
See application file for complete search history.

(56) References Cited

U.S. PATENT DOCUMENTS 5,516,647 A * 5/1996 Husain et al. ................... 435/21

OTHER PUBLICATIONS

"Alkaline phosphatase, serum," May 17, 2006, http://www.labcorp.com/datasets/labcorp/html/chapter/mono/pr014700.htm.
"Diseases of Bioterrorist Potential," UW Northwest Center for Public Health Practice.
Barker and Klose, "Molecular and genetic basis of pathogenesis in *Francisella tularensis*," *Ann. N. Y. Acad. Sci.*, 1105:138-159, 2007.
Baskerville and Hambleton, "Pathogenesis and pathology of respiratory tularaemia in the rabbit," *Br. J. Exp. Path.*, 57:339-347, 1976.
Beisel, "Neutrophile alkaline phosphatase changes in tularemia, sandfly fever, Q fever and noninfectious fevers," *Blood*, 29:257-268, 1967.
Brönnimann et al., "*Listeria monocytogenes* causing solitary liver abscess," *Dig. Surg.*, 15:364-368, 1998.
Dennis et al., "Tularemia as a biological weapon medical and public health management," *JAMA*, 285:2763-2773, 2001.
Dul et al., "EF-4 bacteremia in a patient with hepatic carcinoid," *J. Clin. Microbiol.*, 18:1260-1261, 1983.
Feigin and Dangerfield, "Whole blood amino acid changes following respiratory-acquired *Pasteurella tularensis* infection in man," *J. Infect. Dis.*, 117:346-51, 1967.
Hambleton et al., "Changes in whole blood and serum components during *Francisella tularensis* and rabbit pox infections of rabbits," *Br. J. Exp. Pathol.*, 58:644-52, 1977.
Hambleton et al., "Changes in whole blood and serum components of grivet monkeys with experimental respiratory *francisella tularensis* infection," 59:630-639, 1978.
Lust and Beisel, "Alterations of alkaline phosphatase in mouse tissues after experimental infetion," *Proc. Soc. Exp. Biol. Med.*, 124:812-6, 1967.
Pavlovich and Mishan'kin, "Phosphatase and penicillinase activities as stable traits for the differentiation of the racial classification of *Francisella tularensis*," *Zh. Mikrobiol. Epidemiol. Immunobiol.*, 11-12(Abstract):5-7, 1992.
Safronova et al., "Cytochemical changes in the peripheral blood leukocytes of guinea pigs inoculated against plague, tularemia and anthrax," *Zh. Mikrobiol. Epidemiol. Immunobiol.*, 7(Abstract):73-76, 1982.
Snyder, "Enzyme activities of the livers of mice infected with *Salmonella typhimurium*," *Infect. Immun.*, 4:411-415, 1971.
Woodward and Mayhew, "The host-parasite relationship in tularemia," *J. Bacteriol.*, 71:270-273, 1956.
Woodward et al., "Influence of bacterial infection on serum enzymes of white rats," *App. Microbiol.*, 17:145-149, 1969.
Arise et al., "Cobalt reverses vanadate inhibition of rat kidney alkaline phosphatase," *Scientific Research and Essay*, 3(12):613-620, 2008.
Bentala et al., "Removal of phosphate from lipid A as a strategy to detoxify lipopolysaccharide," *Shock*, 18(6):561-566, 2002.
Butterworth, "The reversible inactivation of pig kidney alkaline phosphatase at low ph," *Biochem. J.*, 108:243-246, 1968.
Dahl et al., "Discovery and validation of a series of aryl sulfonamides as selective inhibitors of tissue-nonspecific alkaline phosphatase (TNAP)," *J. Med. Chem.*, 52:6919-6925, 2009.
Doellgast and Meis, "Use of specific inhibitors to discriminate alkaline phosphatase isoenzymes originating from human liver, placenta and intestine: absence of meconial alkaline phosphatase in maternal serum," *Clin. Chem.*, 25(7):1230-1233, 1979.
Hanford et al., "Alkaline phosphatase protein increases in response to prednisone in HeLa cells," *Biochem. J.*, 200:461-464, 1981.
Kozlenkov et al., "Residues determining the binding specificity of uncompetitive inhibitors to tissue-nonspecific alkaline phosphatase," *Journal of Bone and Mineral Research*, 19(11):1862-1872, 2004.
Lum, "Significance of low serum alkaline phosphatase activity in a predominantly adult male population," *Clin. Chem.*, 41(4):515-518, 1995. Piper et al., "The membrane protein alkaline phosphatase is delivered to the vacuole by a route that is distinct from the VPS-dependent pathway," *The Journal of Cell Biology*, 138(3):531-545, 1997.
Shirazi et al., "Potent inhibition of membrane-bound rat intestinal alkaline phosphatase by a new series of phosphate analogues," *Biochem. J.*, 194:797-802, 1981.
Su et al., "Beneficial effects of alkaline phosphatase in septic shock," *Crit Care Med*, 34(8):2182-2187, 2006.
Tsirel'nikov and Voronina, "Isoforms of alkaline phosphatase from mouse internal organs after bilateral adrenalectomy," *Bulletin of Experimental Biology and Medicine*, 121(3):241, 1996.
Wang et al., "The detection of alkaline phosphatase using an electrochemical biosensor in a single-step approach," *Sensors*, 9:8709-8721, 2009.
Wennberg et al., "Functional characterization of osteoblasts and osteoclasts from alkaline phosphatase knockout mice," *Journal of Bone and Mineral Research*, 15(10):1879-1888, 2000.
Xu et al., "A novel role of alkaline phosphatase in protection from immunological liver injury in mice," *Liver*, 22:8-14, 2002.

\* cited by examiner

*Primary Examiner* — Nita M Minnifield
*Assistant Examiner* — Brian J Gangle
(74) *Attorney, Agent, or Firm* — Fulbright & Jaworski L.L.P.

(57) ABSTRACT

The instant invention concerns *Francisella* bacteria mediated degradation of alkaline phosphatase (AP). Detection of AP degradation may be used to determine the presence of *Francisella* bacteria in a sample. Furthermore, methods for identifying and treating *Francisella* infections by detecting AP degradation are described. Methods of the invention also concerns methods for treating *Francisella* infection by inhibiting AP degradation.

68 Claims, 12 Drawing Sheets

FIG. 1A-C

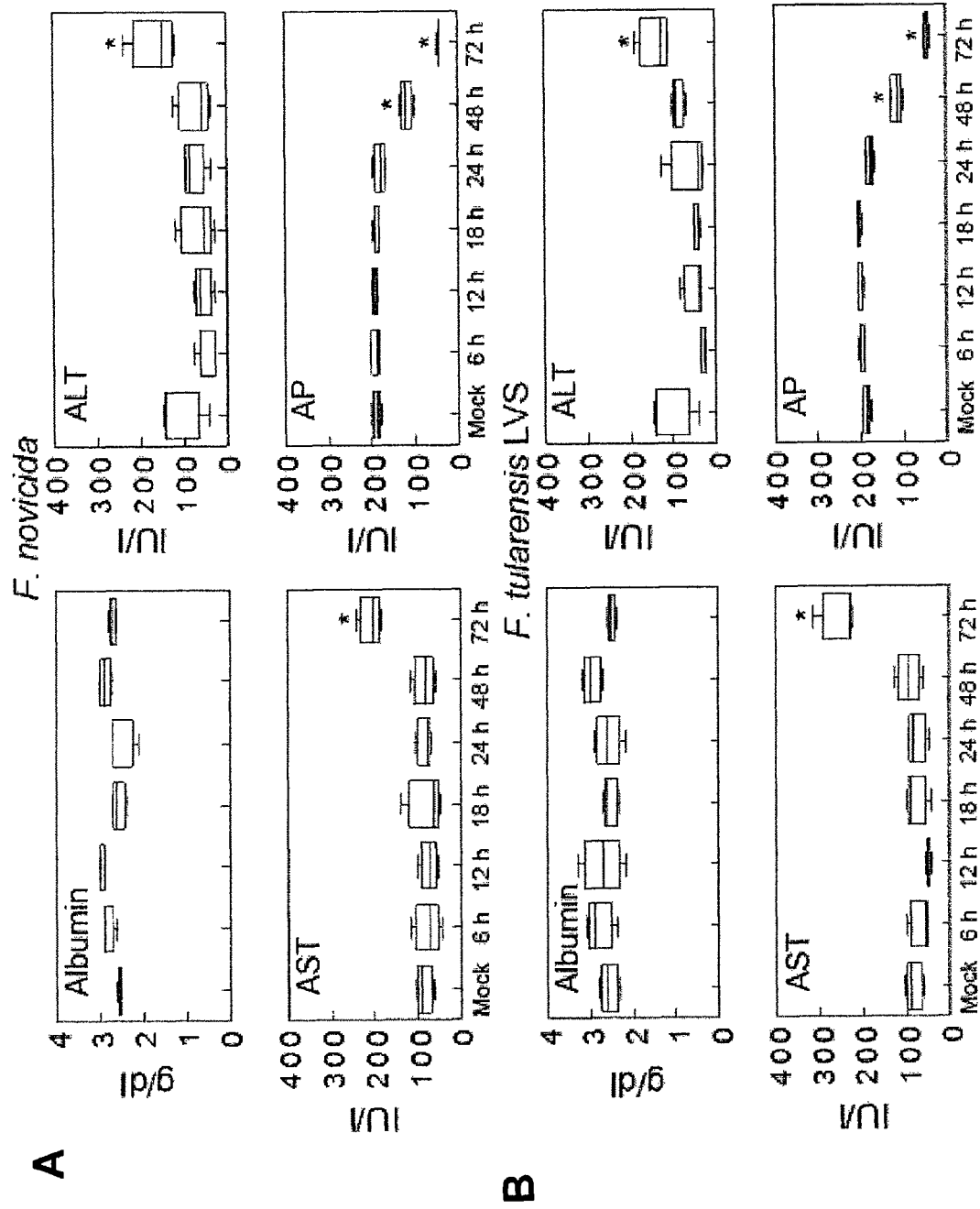
FIG. 2A-B

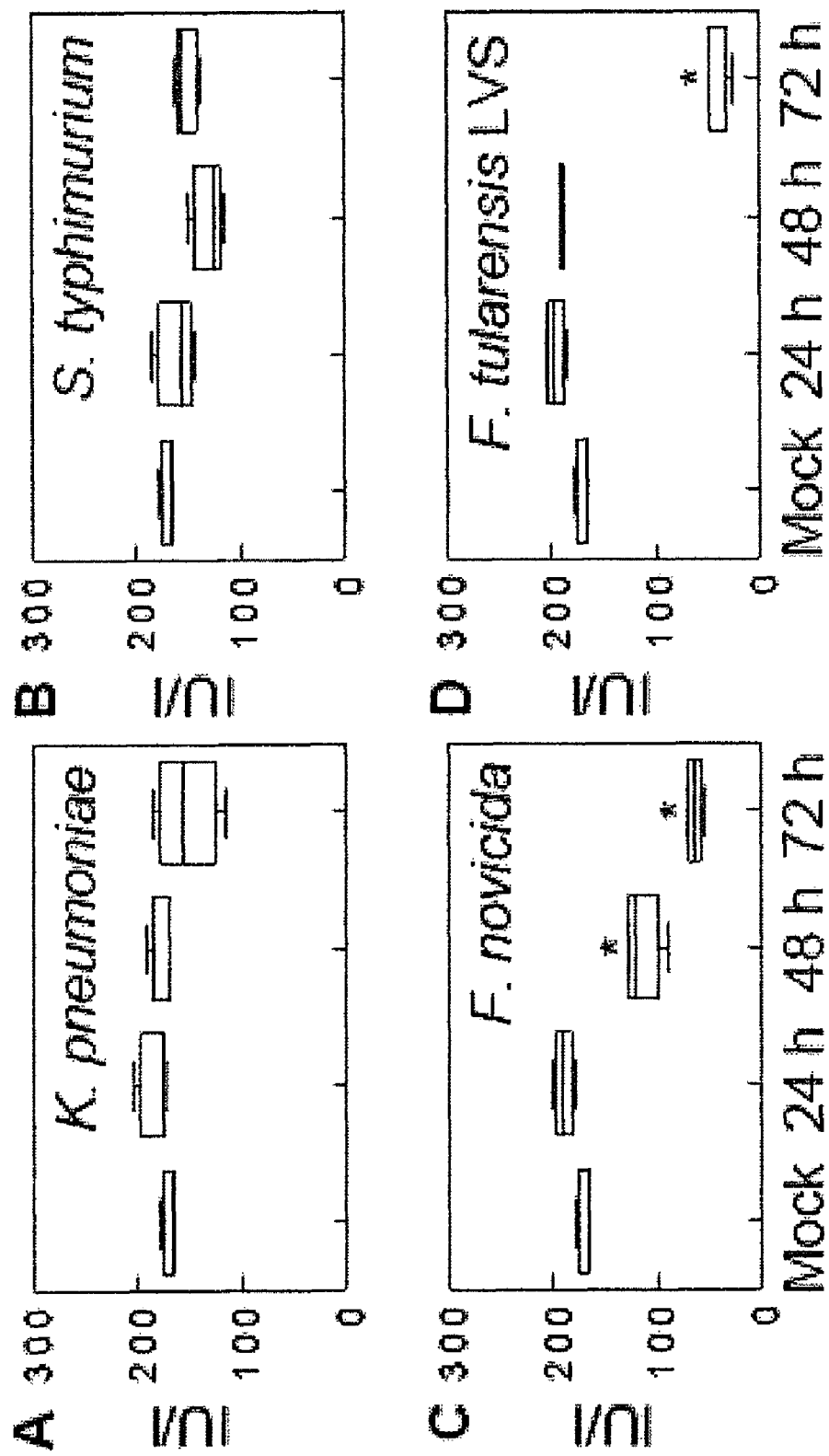
FIG. 3A-D

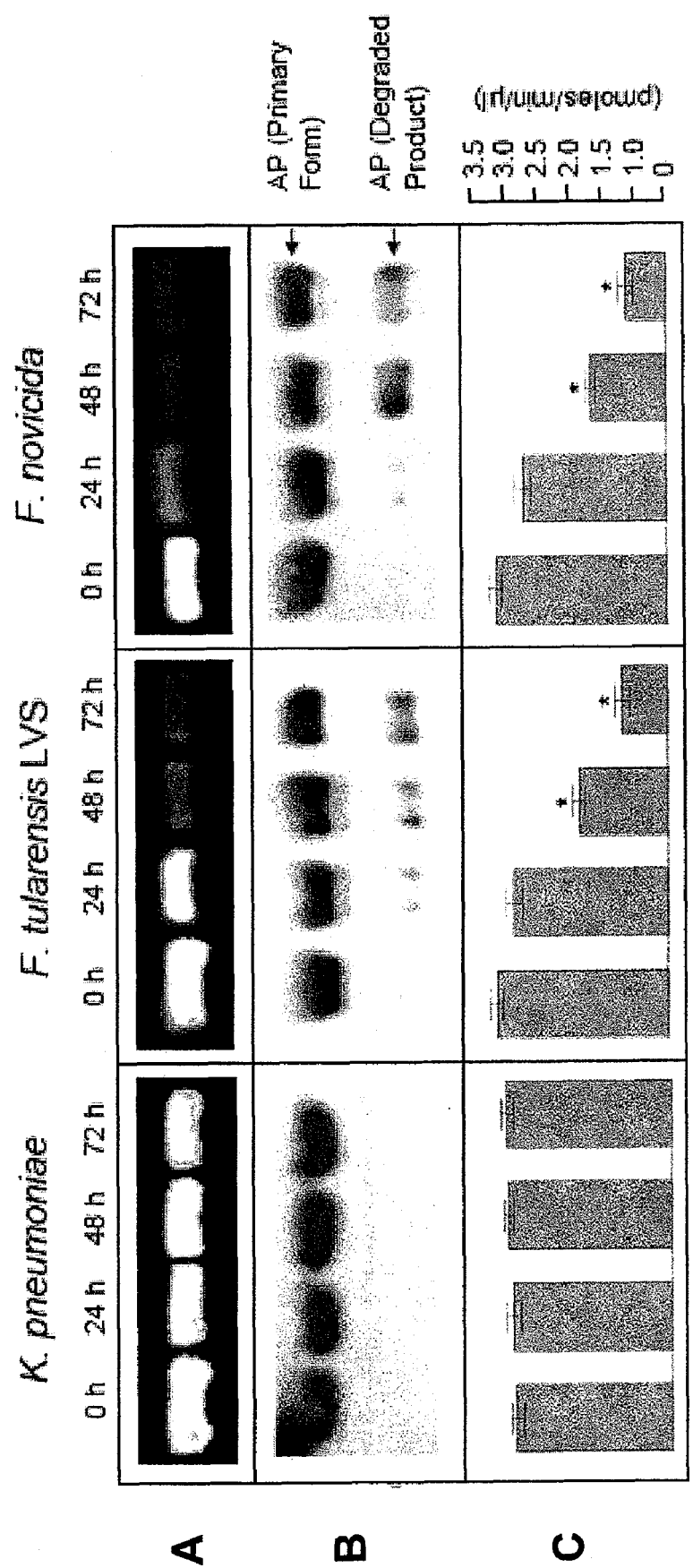
FIG. 4A-C

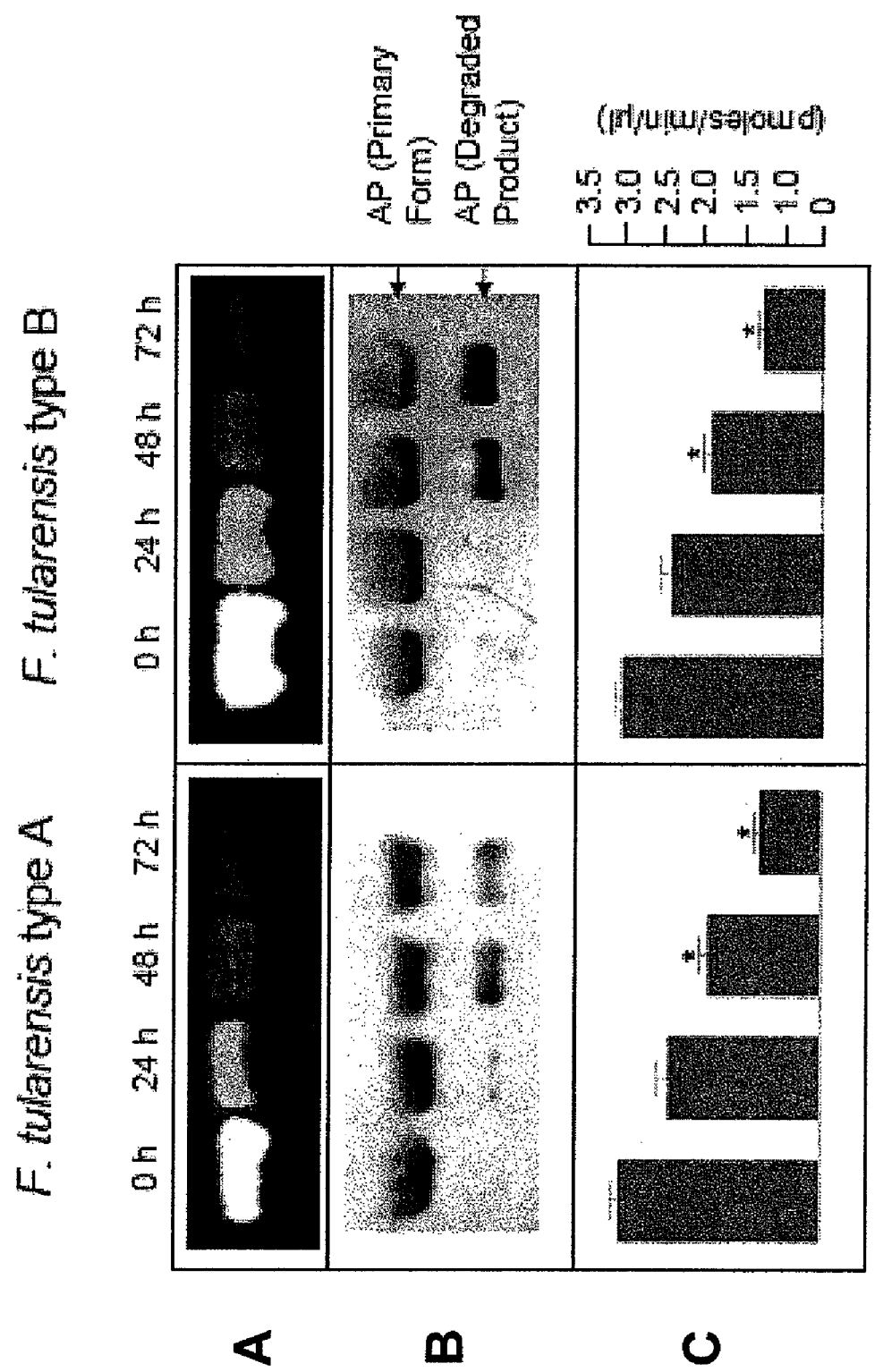
FIG. 5A-C

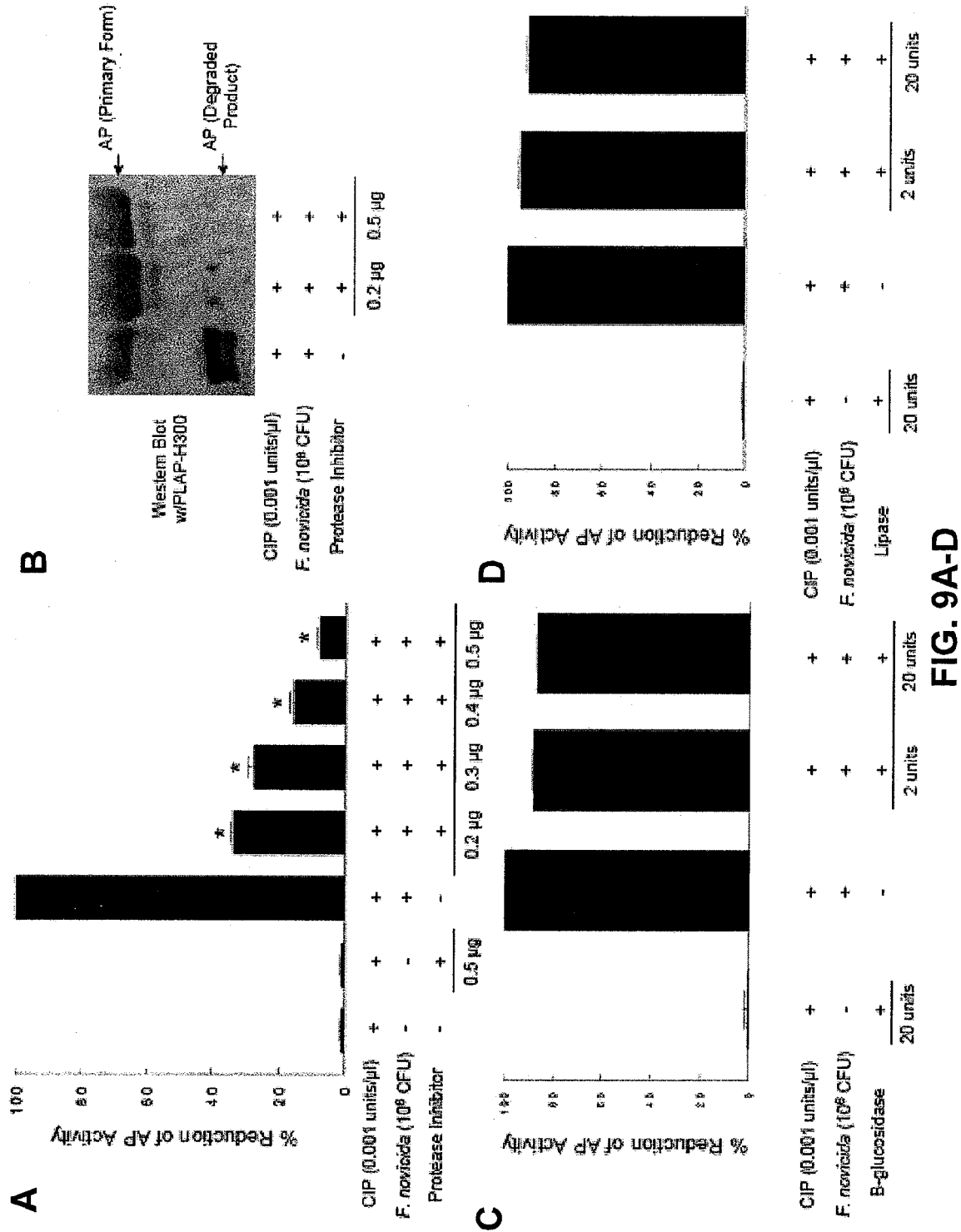
FIG. 9A-D

BIOMARKERS OF *FRANCISELLA* INFECTION

RELATED U.S. APPLICATION DATA

This application claims priority to U.S. Patent Application Ser. No. 60/942,027, filed on Jun. 5, 2007, which is hereby incorporated by reference in its entirety.

The U.S. government may own rights in this invention pursuant to grant number to O1 AI057986 National Institutes of Health.

BACKGROUND OF THE INVENTION

A. Field of the Invention

The present invention concerns methods for detecting *Francisella* bacteria and methods for detecting and treating *Francisella* bacterial infections.

B. Background of the Invention

*Francisella tularensis* is an intracellular Gram negative bacterium that can cause pneumonic tularemia in humans (Ellis et al., 2002; Tarnvik, 1989). *F. tularensis* subsp. *tularensis* is classified as one of the most infectious pathogenic bacteria because inhalation with only a few organisms will cause disease and significant mortality (Saslaw et al., 1961). *F. tularensis* also is considered a potential biological weapon and has been developed as a germ warfare agent by several government programs (Christopher et al., 1997; Dennis et al., 2001; Harris, 1992). Humans infected by *F. tularensis* usually acquire the disease by contact with infected animals, vectors (ticks), exposure to contaminated food and water, or aerosol exposure (Feldman et al., 2001; Tarnvik, 1989).

In experimental animals, *F. tularensis* disseminates and rapidly replicates in systemic organs after pulmonary challenge, leading to host death (Sjostedt, 2003; Conlan et al., 2003; Fortier et al., 1991). The rapid translocation and multiplication of *Francisella*, coupled with the need for early immune recognition (Katz et al., 2006; Malik et al., 2006), may suggest the involvement of bacterial virulence mechanisms that play a role in bacterial spread. However, to date few *Francisella* virulence factors have been identified. Given the rapid spread of *F. tularensis* following infection and the high mortality rate from such infections new methods for treating and rapidly identifying *Francisella* infections are in great need. The present invention answers this long sought need in the art by providing new methods for detecting *Francisella* bacteria and treating *Francisella* infection.

SUMMARY OF THE INVENTION

The present invention overcomes the deficiencies in the art by providing compositions and methods for detection of *Francisella* bacteria. Thus, methods herein describe, in certain embodiments, exploit the finding by the inventors of diagnostic means of detecting *Francisella*.

In a first embodiment there is provided a method for determining the presence of *Francisella* bacteria in a sample comprising detecting alkaline phosphatase (AP) degradation activity in the sample. The term "detecting" as used herein means a qualitative or quantitative assessment of AP degradation activity. "Degradation activity" refers to either or both measurable instability of AP or measurable cleavage of AP. Assays for such measurements are well-known in the art. Protein instability measurements include, e.g., heat or protease degradation experiments as well as other methods known in the art. Protein cleavage (e.g., by a protease) may be measured by methods known in the art, some of which are described herein. The Examples section describes non-limiting methods of detecting AP degradation activity.

As used herein, the term "sample" means any composition that may be tested for bacteria. For example, a sample may be a biological sample, a surface swab, an air sample, a water sample or a food sample. In certain aspects, a sample may be incubated under conditions that are permissive for bacterial replication prior to detecting AP degradation activity. The skilled artisan will recognize that such preincubation may, in some cases, increase the sensitivity of detection. Furthermore, samples of the invention may be concentrated or mixed with appropriate buffers to facilitate AP degradation activity. Other examples of samples are discussed herein, and any example may be used in the methods discussed herein.

Methods herein may be used to detect, e.g., *F. tularensis* and various subspecies thereof such as *F. tularensis* subsp. *tularensis*, *F. tularensis* subsp. *holartica*, *F. tularensis* subsp. *novicida* or *F. tularensis* subsp. *mediasiatica*. Furthermore, since AP degradation activity is specific to *Francisella* bacteria, methods of the invention may be used to determine the presence of a *Francisella* bacteria in a population of other unrelated bacteria. For example, methods of the invention may be used when a population of bacteria comprises or is suspected of comprising *Francisella* bacteria rather than other or similar bacteria such as *K. pneumoniae* or *S. typhimurium*.

As noted, the invention concerns detecting AP degradation activity. There is further provided a method for measuring the amount *Francisella* bacteria in a sample comprising measuring the level of AP degradation activity in the sample. In certain embodiments, the AP degradation activity is an increase in instability in AP. In particular embodiments, AP degradation activity is AP protease activity. Thus, in certain embodiments, methods of detecting AP degradation activity comprise a method of detecting AP protease activity. Methods may comprise, for example, detection of one or more AP degradation products (e.g., an AP protease product, or an AP product that is less stable than the undegraded AP).

As used herein, the term "AP protease activity" refers to an activity that cleaves an AP polypeptide or AP polypeptide fragment into two or more smaller peptides or polypeptides. An AP polypeptide may be, for example, 57.3 kDa tissue non-specific AP (TNAP; liver kidney and bone) human AP (e.g., NCBI accession no. NP_000469), mouse AP (e.g., NCBI accession no. NP_031457) 57 KDa Liver AP, cat AP (e.g., NCBI accession no. XP_535374.2), AP-TNAP, rat AP (e.g., NCBI accession no. NP_037191.1), a bovine AP or a fragment thereof. An AP protease activity may be an AP specific protease activity.

A variety of methods may be used to detect AP degradation activity. For example, in some aspects of the invention a sample (e.g., a serum sample) may comprise AP polypeptides, which may be endogenous or exogenous. In certain of such cases, AP degradation activity may be detected by detecting endogenous AP polypeptide degradation (e.g., cleavage) in the sample. Thus, in certain aspects, detecting *Francisella* bacteria in a sample may comprise (a) obtaining or having a sample comprising an endogenous AP polypeptide and (b) determining whether the AP polypeptide is degraded (e.g., cleaved).

In still further aspects, detecting AP degradation activity in a sample may comprise adding an exogenous AP polypeptide or AP polypeptide fragment to a sample. In certain aspects, the exogenous AP polypeptide or AP polypeptide fragment is used as a substrate for AP degradation. The exogenous AP polypeptide or AP polypeptide fragment may be degraded such as via proteolysis, in certain embodiments. AP polypeptides may be from an AP from a variety of animals and may be an AP isoform expressed any particular tissues. However, in certain preferred embodiments the AP is a mammalian AP such as an AP that is expressed in the liver. AP polypeptides for use as substrates may be for example purified or recombinant human AP (e.g., NCBI accession no. NP_000469), mouse AP (e.g., NCBI accession no. NP_031457), cat AP (e.g., NCBI accession no. XP_535374.2), rat AP (e.g., NCBI accession no. NP_037191.1), cow AP or a fragment thereof. Furthermore, AP degradation substrates may be purified or recombinant peptides or polypeptides. It is contemplated that when exogenous AP is used to detect AP degradation activity the exogenous AP and sample will be mixed and incubated under conditions that are permissive for AP degradation. Suitable conditions for such incubations are further described in the detailed description and the examples.

Methods for detecting AP and AP polypeptide degradation are well known in the art. For example, an antibody that binds to AP may be used to detect stable and/or intact versus degraded AP polypeptides. As used herein the term "antibodies" refers to antibodies and antibody fragments such as polyclonal antibodies (including but not limited to peptide antibodies), monoclonal antibodies, humanized antibodies, single chain antibodies and fragments thereof. For example, AP degradation may be detected by binding of an antibody to an AP or AP polypeptide that has reduced mass or increased gel mobility (e.g., via Western blot as demonstrated herein). In still further cases, antibodies that bind to specific portions of AP (such as monoclonal or peptide antibodies) may be employed. For instance, AP from a sample may be immobilized in an ELISA assay with an antibody that binds to the amino or carboxyl terminus of the polypeptide, incubated with a sample and then the AP or AP polypeptide detected using a second antibody that binds to the opposite end of the polypeptide. In this case, AP degradation activity (e.g., AP protease activity) would be indicated by a reduced binding of the second AP-binding antibody due to degradation (e.g., a release of an AP cleavage fragment). Furthermore, it is contemplated that antibodies that specifically bind to an AP degradation product (e.g., a degraded AP or an AP cleavage product) but have reduced affinity for intact AP may be used to detect AP degradation (e.g., AP cleavage).

In certain aspects of the invention, AP degradation activity is detected by the addition of exogenous AP to a sample. In some cases, exogenous AP may be labeled to facilitate the detection of AP cleavage. A labeled AP may, for instance, comprise a fluorescent, calorimetric, enzymatic, or radioactive label. Furthermore, in cases where recombinant a AP substrate is used, the substrate may comprise a fusion protein on the amino or carboxyl terminus that aids in detection of AP degradation. For example, labeled exogenous AP may be immobilized (e.g., by binding to an immobilized antibody or via a fused polypeptide with a specific binding affinity), incubated with a sample and AP degradation activity may be assessed by release of labeled AP polypeptide fragments. In another example, an AP protease substrate may comprise a fluorophore and quenching agent separated by a AP polypeptide sequence. In this aspect AP degradation activity may be detected by a increase in fluorescence due to release of the quenching agent. Furthermore, in certain aspects AP degradation may be detected in a sample by detecting AP cleavage products by mass spectrometry.

In still further aspects, AP degradation activity in a sample may be assessed by detecting a loss in AP activity after incubating exogenous AP enzyme with a sample. In this case recombinant or purified active AP enzyme may be incubated with a sample under conditions that are permissive for degradation. Following or during incubation the activity of the enzyme is assessed wherein loss of activity is indicative of degradation. As outlined above, a variety of purified or recombinant AP enzymes may be used according to the invention. In some cases an AP enzyme may be calf-intestinal alkaline phosphatase (CIP). Methods for assessing AP activity are well known in the art and further exemplified herein. A loss of AP activity may refer to, e.g., a decrease in activity of about, at least about, or at most about 5%, 10%, 15%, 20%, 25%, 30%, 35%, 40%, 45%, 50%, 55%, 60%, 65%, 70%, 75%, 80%, 85%, 90%, 99%, or 100%, or any range derivable therein.

In a further embodiment there is provided a method for determining whether a subject has a *Francisella* infection comprising (a) obtaining a sample from a subject and (b) detecting alkaline phosphatase (AP) degradation activity in the sample wherein AP degradation activity is indicative *Francisella* infection. In these or other embodiments a sample may comprise any biological sample from a subject such as a tissue biopsy sample, a throat or nasal swab, or a blood sample. For example, in certain cases the sample may be a lung or liver biopsy sample (i.e., comprising lung or liver cells) or a serum sample. As described herein, in certain aspects a sample from a subject may be incubated under conditions that are permissive for bacterial growth prior to detecting AP degradation activity. Furthermore, there is provided a method for treating a subject with an infection comprising (a) obtaining a sample from a subject (b) detecting alkaline phosphatase (AP) degradation activity in the sample wherein AP degradation activity is indicative *Francisella* infection and (c) treating the subject with an antibiotic that is effective against *Francisella* infection or another drug depending on whether AP degradation activity is detected.

It is contemplated that methods for determining or diagnosing a *Francisella* infection in a subject will typically involve a living human subject. However, methods of the invention may be used to assess the presence of *Francisella* bacteria in deceased subjects and may for example be used for rapid assessment when *Francisella* is suspected as the cause of death. Furthermore, methods of the invention may be used to determine whether non-human animals have *Francisella* infection. Such methods may be used to monitor and contain outbreaks of infection for instance in game animals (e.g., deer) or in arthropod vectors such as deer flies and ticks. Thus, in some aspects, the invention provides a method for determining the prevalence of a *Francisella* infection in a population comprising (1) obtaining or having a plurality of samples from the population and (2) detecting AP degradation activity in the plurality of samples.

In some cases a subject according to the invention is further defined as a subject that has been exposed to *Francisella* bacteria. As used herein the term "exposed" means a subject that has been in close proximity to a subject known to have a *Francisella* infection (e.g., in the same room as, or sharing objects touched by the subject known to have the infection) or a known source of *Francisella* bacteria (e.g., laboratory samples). In this case, a sample will preferably be taken from the exposed or possibly exposed subject about 8, 12, 24, 36 or 48 hours to about 48, 60 or 72 hours after exposure, or any range derivable therein. Furthermore, in some cases samples will be taken at 2, 3, 4, 5, 6, 7, 8, 9, 10 or more different times (or any range derivable therein) in order to determine if there is an increase in AP degradation activity over time. Furthermore, a subject of the invention may be defined as a subject that presents with symptoms that that are consistent with *Francisella* infection. Thus, methods of the invention may be used along with other clinical criteria to either confirm or exclude *Francisella* infection as a diagnosis and determine a course of treatment.

It will be understood that in some aspects of the invention, a sample need not be directly obtained from a subject for the methods of the invention. For example, in some cases a sample may be collected by a third party such as a hospital worker and sent to a laboratory for assessment of AP degradation activity. Thus, in some aspects a method of the invention comprises (a) having a sample from a subject and (b) detecting alkaline phosphatase (AP) degradation activity in the sample wherein AP degradation activity is indicative *Francisella* infection. Furthermore, a method of the invention may also be defined as a method for assisting in determining whether a subject has a *Francisella* infection comprising (a) obtaining or having a sample from a subject, (b) detecting AP degradation activity in the sample and (c) reporting information regarding AP degradation activity in the sample. As further elucidated above detecting AP degradation activity in a subject (or a sample from the subject) may be used to determine a method for treating the subject.

In still further embodiments there is provided a method for monitoring the effectiveness of a therapy for *Francisella* infection in a subject comprising (a) obtaining a sample from the subject and (b) detecting AP degradation activity in the sample wherein AP degradation activity is indicative *Francisella* infection. In this aspect of the invention samples may be taken 2, 3, 4, 5, 6, 7 or more times (or any range derivable therein) during the course of therapy administration. Thus, a decrease in AP degradation activity over the course of therapy administration may be indicative of the effectiveness of the therapy. On the other hand, if AP degradation activity does not decrease or increases over the course of therapy then a lack of efficacy is indicated. In the case where a lack of efficacy is indicated a second therapy may be administered such as different antibiotic of a different class of antibiotic.

As exemplified herein *Francisella* infection causes liver damage and results in an increase of liver specific enzymes into the blood. Interestingly, this indicates that while serum AP activity drops during *Francisella* infection overall serum AP polypeptide levels rise. Thus, in certain aspects there is provided a method for determining whether a subject has a *Francisella* infection comprising (a) obtaining or a having a blood sample from the subject and (b) determining the AP activity and AP polypeptide levels in the sample wherein a decrease in AP activity relative to AP protein levels is indicative of *Francisella* infection. In some aspects, the ratio between AP activity and AP levels in serum may be compared to a standard level obtained by assessing AP activity and AP levels in an uninfected person. Thus, a standard may be established that can be compared to the test results from any particular sample. Furthermore, in certain cases, having or obtaining a sample from a subject may comprise obtaining 2 or more samples at different times. In this case *Francisella* infection may be indicated by a decrease in AP activity over time and an increase in AP serum levels over time.

In still further embodiments there is provided a method for treating a *Francisella* infection in a subject comprising reducing or inhibiting AP degradation activity in the subject. As used herein treating a *Francisella* infection in a subject may comprise preventing or delaying the onset of disease symptoms from *Francisella* infection. A variety of methods may be used to reduce or inhibit AP degradation activity. For example, in certain aspects an effective amount of a protease inhibitor may be administered to the subject. In this aspect an effective amount of such an inhibitor may reduce AP cleavage in the subject or reduce AP degradation activity in samples from the subject as assessed by any of the methods described herein. Some specific examples of protease inhibitors include but are not limited to small molecule protease inhibitors, peptide or modified peptide inhibitors (e.g., peptide that are homologous to the AP cleavage site), antibodies that bind to AP and prevent cleavage and antibodies that bind to a *Francisella* AP factor (e.g., protease). In is further contemplated that protease inhibitors of the invention may be administered to a subject prophylactic in cases where a subject is a risk for *Francisella* infection. Such inhibitors may be administered up to, e.g., 72 hours (e.g., 8, 12, 18, 24, 36, 48, 60, or more, or any range derivable therein) before the subject is exposed to conditions comprising or suspected to comprise *Francisella* infection.

In still a further embodiment there is provided a method for determining or estimating the effectiveness of a *Francisella* vaccine composition in a subject comprising (a) administering the vaccine composition to the subject one or more times, (b) administering a live (or live attenuated) *Francisella* bacteria to the subject, (c) obtaining a sample for the subject and (d) determining the amount of AP degradation activity in the sample. The skilled artisan will recognize that in the foregoing methods a live *Francisella* bacteria is defined as a bacteria that is capable of reducing serum AP activity in an unvaccinated subject (e.g., capable of producing AP degradation activity during infection). Any of the methods for determining AP degradation activity described herein may be used in the foregoing methods. As described herein a reduced level of AP degradation activity in the subject relative to an unvaccinated subject is indicative of vaccine efficacy. In certain cases, a vaccine composition for use in the current method is a live attenuated *Francisella* bacterial composition such as *F. tularensis* live vaccine strain (LVS). In certain aspects, methods of the invention may be used to determine an effective amount of a vaccine composition or an effective number of administrations to provided enhanced immunity. Thus, in some embodiments, the invention provides a method for quantitatively or semi-quantitatively evaluating the efficacy of a *Francisella* vaccine composition in an animal model by measuring AP activity following live *Francisella* bacterial challenge. As described herein, AP activity may be measured at various times following challenge, such as about 1, 2, 3, 4 or 5 days post challenge. Such methods may be of particular use when comparing the relative efficacy of a number (i.e., two or more) of candidate vaccine compositions for example in cases where each candidate vaccine protects animals from lethal challenge. In this case, the measurement of AP activity post-challenge may be used to indicate more subtle advantages of one vaccine composition over another in cases where survival analysis fails to elucidate such differences.

In still a further embodiment there is provided a method for identifying an attenuated *Francisella* bacteria comprising screening a population of *Francisella* bacteria for bacteria that have reduced AP degradation activity. Thus, it is contemplated that such methods may be used to identify attenuated *Francisella* bacteria comprising reduced or essentially lacking AP degradation activity. Such bacteria may further be incorporated into vaccine compositions.

In certain embodiments, AP degradation activity is caused by a *Francisella* associated degradation factor. Accordingly, methods of the present invention contemplate methods of detecting the activity of this factor. Any method discussed herein may comprise this detection method, and this method may be used as a substitute for or in addition to detecting AP degradation activity. For example, a method may comprise determining whether a subject has a *Francisella* infection comprising detection of increased activity of this factor in a sample relative to a sample known not to comprise *Francisella*, wherein increased activity of the factor is indicative of *Francisella* infection. The factor may be a *Francisella* associated protease. Antibodies, as discussed herein, may bind to such a protease. The factor (e.g., a protein) may increase the instability of AP. The factor may be a protein involved in a secretion pathway, such as a pathway that ClpV and VgrG genes are involved, as described herein and as is known in the art. The factor may be on the surface of a protein involved in this pathway.

It is contemplated that any embodiment discussed in this specification can be implemented with respect to any method or composition of the invention, and vice versa. Furthermore, compositions of the invention can be used to achieve methods of the invention.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings are part of the present specification and are included to further demonstrate certain aspects of the present invention. The invention may be better understood by reference to the drawings in combination with the detailed description of specific embodiments presented herein.

FIG. 1A-C: Extracellular bacterial dissemination after pulmonary *F. tularensis* challenge. FIG. 1A, BALB/c mice (3 per group) were challenged i.n. with 400 CFU of either *F. novicida* or *F. tularensis* LVS. The lungs and livers of infected animals were removed at 24 h, 48 h, and 72 h post challenge, homogenized, and plated for bacterial enumeration. The colonies were enumerated after 24-36 h of incubation at 37° C. Dashed lines indicate bacterial levels in the liver while solid lines indicate bacterial levels in the lungs. FIG. 1B, BALB/c mice (3 per group) were challenged i.n. with 400 CFU of *F. novicida*. Mice were bled at 24 h, 48 h, and 72 h post challenge, and plasma was prepared and plated for bacterial enumeration. FIG. 1C, the *F. novicida* (solid lines and circles) or mock, PBS infected plasma (dashed lines with triangles) (200 µl) was passively transferred to naïve BALB/c mice (6 per group) via i.p. injection. The animals were weighed daily and monitored for morbidity and mortality. Significant differences were observed in survival and weight loss in mice receiving infected versus mock plasma (P=0.0002, Kaplan-Meier test). Results are representative of two independent experiments.

FIG. 2A-B: Plasma AP activity decreases following pulmonary *F. tularensis* challenge. BALB/c mice (3 per group) were challenged i.n. with 400 CFU of either (FIG. 2A) *F. novicida* or (FIG. 2B) *F. tularensis* LVS. Mice were bled at the corresponding intervals, and plasma was prepared. Albumin content, as well as ALT, AST and AP activity levels in *Francisella* infected plasma were measured using an Olympus AU640e Chemistry Immuno Analyzer and reported as either IU/l (international units/liter) or g/dl (grams/deciliter). Mean values±SEM are shown for all experiments. Asterisks indicates significant differences between indicated groups (P<0.001, Student's t test). Results are representative of four independent experiments.

FIG. 3A-D: The inhibition of plasma AP activity was specific to pulmonary *Francisella* exposure. BALB/c mice (3 per group) were challenged i.n. with 400 CFU of either *K. pneumoniae* (FIG. 3A), *S. typhimurium* (FIG. 3B), *F. novicida* (FIG. 3C), or *F. tularensis* LVS (FIG. 3D). Mice were bled at 24 h, 48 h, and 72 h post challenge, and plasma was prepared. The infected and mock plasma AP concentrations were measured and reported as IU/l. AP activity levels in the plasma were measured using an Olympus AU640e Chemistry Immuno Analyzer. Mean values±SEM are shown for all experiments. Asterisks indicate significant differences between indicated groups (P<0.001, Student's t test). Results are representative of three independent experiments.

FIG. 4A-C: Zymogram and Western blot analyses of AP activity following pulmonary *K. pneumoniae*, *F. tularensis* LVS and *F. novicida* challenge. BALB/c mice (3-5 per group) were challenged i.n. with 400 CFU of either *F. novicida*, *F. tularensis* LVS, or *K. pneumoniae*. Mice were bled at 24 h, 48 h, and 72 h post challenge, and plasma was prepared. FIG. 4A, 4-MUP zymogram analyses of AP activity in plasma. FIG. 4B, Western blot analyses of plasma using an anti-mouse AP (PLAP-H300) antibody, which detects all isoforms of AP. FIG. 4C, the AP activity of plasma measured fluorometrically with 4-MUP and reported as pmoles/min/µl. Mean values±SEM are shown for all experiments. Asterisks indicate significant differences between indicated groups (P<0.001, Student's t test). Results are representative of three independent experiments.

FIG. 5A-C: Zymogram and Western blot analyses of AP activity following pulmonary *F. tularensis* type A and type B challenge. BALB/c mice (3-5 per group) were challenged i.n. with 100 CFU of either *F. tularensis* type A or type B. Mice were bled at 24 h, 48 h, and 72 h post challenge, and plasma was prepared. FIG. 5A, 4-MUP zymogram analyses of AP activity in plasma. FIG. 5B, Western blot analyses of plasma using an anti-mouse AP (PLAP-H300) antibody, which detects all isoforms of AP. FIG. 5C, the AP activity of plasma measured colorimetrically with 4-MUP and reported as nmoles/min/μl. Mean values±SEM are shown for all experiments. Asterisks indicate significant differences between indicated groups (P<0.001, Student's t test). Results are representative of three independent experiments.

FIG. 7A-C: Inhibition of AP activity in hepatocytes and identification of the liver isoform of AP in plasma after *F. tularensis* infection. FIG. 7A-B, the livers of normal BALB/c mice were perfused, removed, and single cell suspensions were prepared. Primary hepatocytes were seeded at $5 \times 10^5$ cells/well, infected with *F. novicida*, *F. tularensis* LVS (MOI of 10:1 or 100:1), or medium alone for 1 h, then treated for an additional 1 h with medium containing gentamicin, and subsequently cultured with medium alone. The cells were washed with Hank's Balanced Salt Solution containing 0.1% gelatin and lysed in 0.2% deoxycholic acid sodium salt. Cell supernatants (FIG. 7A) and cell lysates (FIG. 7B) were collected at various intervals and analyzed fluorometrically with 4-MUP for AP activity. The results are reported as percent inhibition of AP activity, as compared to mock-infected hepatocytes. FIG. 7C, BALB/c mice (3 per group) were challenged i.n. with 400 CFU of *F. novicida*. The animals were bled at 24 h, 48 h, and 72 h post challenge, plasma was prepared, and Western blot analyses were performed using an anti-mouse AP (TNAP-N18) antibody, specific for the liver isoform of AP. CIP was used as a specificity control. Mean values±SEM are shown for all experiments. Asterisks indicate significant differences between indicated groups (P<0.001, Student's t test). Results are representative of three independent experiments.

FIG. 8A-C: Inhibition of AP activity requires replicating *F. tularensis*. FIG. 8A-B, normal BALB/c plasma was incubated individually with each of the following: FIG. 8A, $1 \times 10^6$ CFU of live, heat-killed, or sonicated *F. novicida*, $1 \times 10^6$ CFU of live, heat-killed, or sonicated *F. tularensis* LVS, or $1 \times 10^6$ CFU of live *K. pneumoniae*. FIG. 8B, $1 \times 10^6$ CFU of live *F. novicida*, 10-20 μg of *F. novicida* LPS, 10-20 μg of *F. tularensis* LVS LPS, or 10-20 μg of *E. coli* LPS. Samples were incubated for 24 h and 48 h at 37° C. with gentle rotation and analyzed fluorometrically for AP activity with 4-MUP. The results are reported as % inhibition of AP activity, as compared to mock-infected hepatocytes. FIG. 8C, Western blot analysis of normal plasma incubated with $1 \times 10^6$ CFU of either live or heat killed *F. novicida* using an anti-mouse AP (PLAP-H300) antibody. Mean values±SEM are shown for all experiments. * Significant differences between indicated groups (P<0.001, Student's t test). Results are representative of three independent experiments.

FIG. 9A-D: Inhibition of AP activity is mediated by *F. tularensis* protease(s). FIG. 9A, CIP (0.001 units/μl) was incubated with either $1 \times 10^6$ CFU of *F. novicida* or *F. novicida* combined with varying concentrations of a protease inhibitor. Samples were incubated for 48 h at 37° C. with gentle rotation and analyzed fluorometrically for AP activity using 4-MUP. The results are reported as % reduction of AP activity, as compared to CIP incubated with bacteria alone. FIG. 9B, Western blot analyses of CIP (0.001 units/μl) incubated with *F. novicida*±protease inhibitor and probed with anti-mouse AP (PLAP-H300) antibody. FIG. 9C-D, CIP (0.001 units/μl) was incubated with either $1 \times 10^6$ CFU of *F. novicida* alone, or *F. novicida* combined with varying concentrations of β-glucosidase (FIG. 9C) or lipase (FIG. 9D). Samples were incubated for 48 h at 37° C. with gentle rotation and analyzed fluorometrically for AP activity using 4-MUP. The results are reported as % reduction of AP activity, as compared to samples incubated with bacteria alone. Mean values±SEM are shown for all experiments. * Significant differences between indicated groups (P<0.001, Student's t test). Results are representative of three independent experiments.

FIG. 10A, A graph indicating mortality in the three groups of vaccinated animals. FIG. 10B, shows a graph of serum AP activity in the three groups of mice at 0, 1, 2, 3, 7 and 14 days post challenge.

DESCRIPTION OF ILLUSTRATIVE EMBODIMENTS

Figure 6:
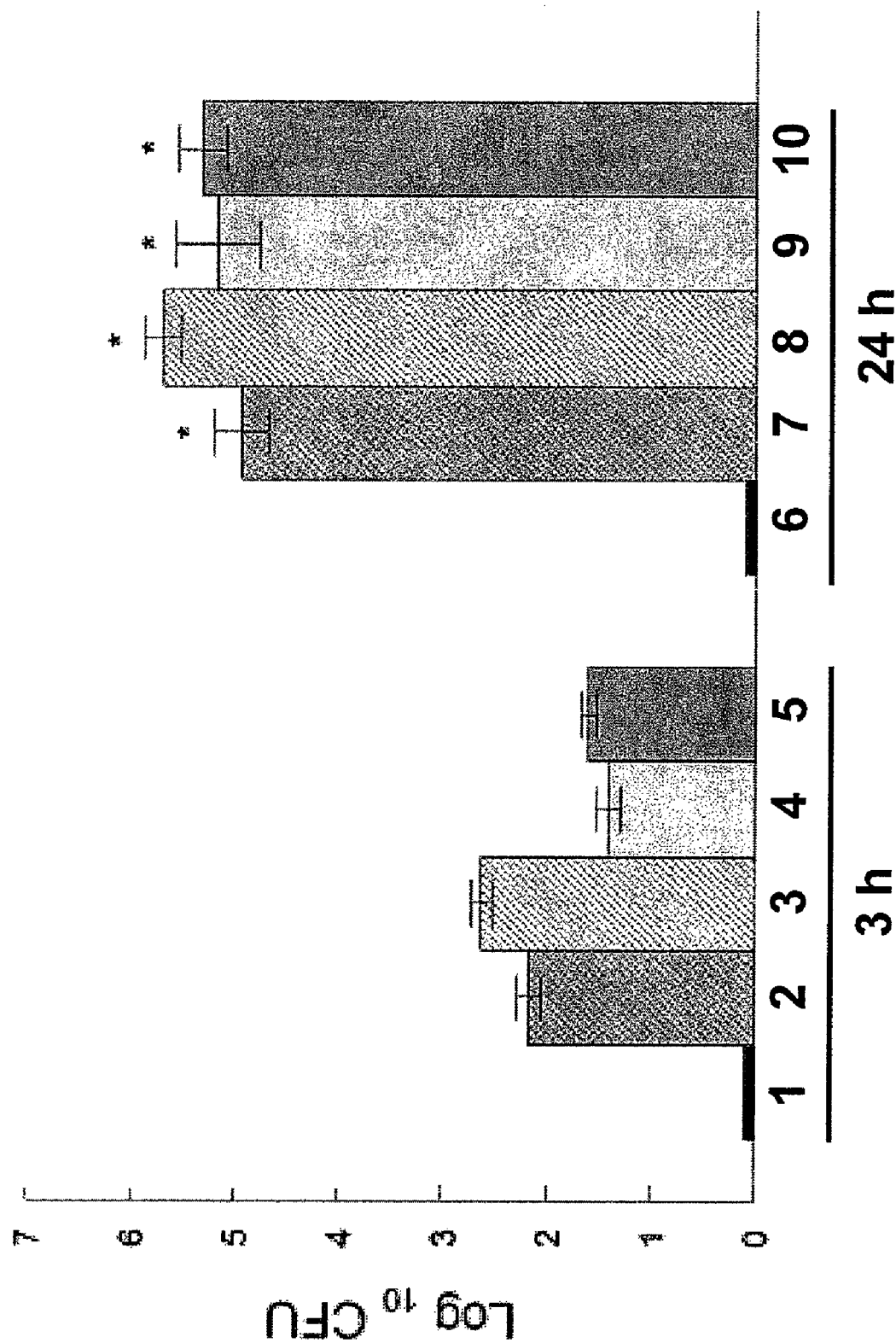
FIG. 6: Replication of *F. tularensis* in infected hepatocytes. The livers of normal BALB/c mice were harvested, removed, and single cell suspensions were prepared. Primary hepatocytes were seeded at $5 \times 10^5$ cells/well, mock infected (columns 1 and 6) infected with *F. novicida* at MOI 10:1 (columns 2 and 7), *F. novicida* at MOI 100:1 (columns 3 and 8), *F. tularensis* LVS MOI of 10:1 (columns 4 and 9) or *F. tularensis* LVS MOI 100:1 (columns 5 and 10). Following infection cells were treated for an additional 1 h with medium containing gentamicin, and subsequently cultured with medium alone. The cells were washed with Hank's Balanced Salt Solution containing 0.1% gelatin and lysed in 0.2% deoxycholic acid sodium salt. All samples were plated on TSA (+0.1% cystein) plates, and colonies were enumerated after 24-36 h of incubation at 37° C. Mean values±SEM are shown for all experiments. Asterisks indicate significant differences between indicated groups (P<0.001, Student's t test). Results are representative of three independent experiments.

*F. tularensis* subsp. *tularensis* is classified as one of the most infectious pathogenic bacteria because inhalation with only a few organisms will cause disease and significant mortality (Saslaw et al., 1961). *F. tularensis* also is considered a potential biological weapon and has been developed as a germ warfare agent by several government programs (Christopher et al., 1997; Dennis et al., 2001; Harris, 1992). In this regard, the respiratory tract and lungs are major portals of entry for inhalation exposure and serve as primary sites of infection before systemic spread. Aerosol exposure to *F. tularensis* leads to high levels of morbidity and mortality thus new methods for rapidly diagnosing and treating *F. tularensis* infection are in great need.

Previously, it has been observed that serum AP activity unexpectedly drops during the course of *Francisella* infection. However, the cause or significance of these observations were not clear. The studies described herein demonstrate that a *Francisella*-associated protease specifically cleaves serum AP thereby reducing its activity. Importantly, the *Francisella* mediated AP cleavage is specific to *Francisella* bacterial infection and is not observed during other gram negative bacterial infections (see FIGS. 3, 4). AP cleavage products may be detected at 24 hours post-infection ore earlier suggesting that AP cleavage may constitute an early diagnostic marker of infection. Furthermore, *Francisella* associated AP cleavage could be prevented by protease inhibitors indicating that such inhibitors may be used to prevent AP cleavage in vivo thereby reducing or delaying the pathogenesis of infection. Thus, the se new studies identify a novel *Francisella*-associated AP protease activity and provide new methods for treating and identifying *Francisella* infection.

The new methods provided herein highly advantageous relative to previous methods for identifying an *F. tularensis* infection since simple molecular biological diagnostic assays (e.g., ELISA) may be used shortly after infection to detect AP cleavage products. Furthermore, the ease of these techniques enables their use in monitoring the effectiveness of anti-*Francisella* therapy. Thus, AP protease activity may be monitored over the course of infection to determine the effectiveness of a therapy or assess the progression of disease. Furthermore, AP protease activity may be inhibited by the therapeutic administration of protease inhibitors thereby reducing the severity of *Francisella* associated disease. Hence, methods of the invention offer a new target (AP protease) that may be exploited to diagnose and treat *F. tularensis* infection.

These and other aspects of the present invention are described in further non-limiting detail in the following sections.

I. AP Polypeptides

As described in the foregoing summary, some aspects the invention concern AP polypeptides and polypeptide fragments. These AP polypeptides may be present in a sample or exogenous polypeptides added to a sample to assess AP degradation activity in the sample. AP polypeptides for use in the current invention include, but are not limited to, human liver AP (NCBI accession no.NP_000469), mouse liver AP (NCBI accession no. NP_031457), cat liver AP (NCBI accession no. XP_535374.2), rat liver AP (NCBI accession no. NP_037191.1), a bovine AP such as calf-intestinal AP or a fragment thereof. For instance an AP polypeptide sequence for use according to the current invention may comprise an AP that at least 70%, 80%, 90%, 95%, 98% or more identical to human liver AP and/or other mammalian AP sequences. Thus, in certain aspects of the invention an AP may be a human AP sequence wherein one or more amino acid has been substituted for an amino acid at a corresponding position of another mammalian AP polypeptide.

In additional aspects of the invention, AP polypeptides may be further modified by one or more amino substitutions while maintaining their ability to be degraded (e.g., rendered less stable, or cleaved) by a *Francisella*-associated protease. Any of the methods described herein may be used to determine whether any particular modified AP is, for example, cleaved by *Francisella*-associated AP protease and such routine screening is well within the skill level of those in the art. For example, modified AP polypeptides may comprise amino acid substitutions can be made at one or more positions wherein the substitution is for an amino acid having a similar hydrophilicity. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in AP and will likely only have minor effects on their activity and/or ability to be cleaved by protease. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the AP polypeptides described herein may be modified by the substitution of an amino acid, for different, but homologous amino acid with a similar hydrophilicity value. Amino acids with hydrophilicities within +/−1.0, or +/−0.5 points are considered homologous.

Furthermore, it is envisioned that AP sequences may be modified by amino acid deletions, substitutions, additions or insertions. Such modified AP polypeptides may be screened to determine whether they may still be cleaved by *Francisella*-associated protease. Furthermore, modified AP polypeptides may be screened to determine whether they maintain the AP enzymatic activity.

In some aspects the invention concerns AP polypeptide fragments. It will be understood that such AP fragment may comprise amino terminal, carboxyl terminal or internal deletions of AP polypeptide sequence. In some aspects such fragments may be screened to determine whether they may be cleaved by a *Francisella*-associated protease. Such methods may involve making progressively larger deletions in an AP polypeptide and determining whether the AP fragment may be cleaved by a *Francisella*-associated protease. Thus, in some aspects an AP fragment for use in the invention is A polypeptide fragment that comprised a *Francisella*-associated protease cleavage site.

II. Methods for Producing Antibodies

As described above certain aspects of the invention involve the use of antibodies. For example, in some aspects an antibody may be a AP binding antibody that may be used to detect AP degradation activity, such as via detection of an AP degradation fragment, such as an AP cleavage fragment. In certain other aspects and AP binding antibody may bind to AP thereby preventing *Francisella*-associated protease cleavage and thus acting as a protease inhibitor. Antibodies may be made by any of the methods that as well known to those of skill in the art. Furthermore, antibodies may be generated that bind to a *Francisella*-associated AP protease. The following methods exemplify some of the most common antibody production methods. The skilled artisan will recognize that the methods provided here may be used to generate antibody that binds a particular portion an antigen. Thus, in certain aspects an antibody may be generated that binds to a amino or Carboxyl terminal AP cleavage product that results from *Francisella*-associated protease cleavage.

A. Polyclonal Antibodies

Polyclonal antibodies generally are raised in animals by multiple subcutaneous (sc) or intraperitoneal (ip) injections of the antigen. As used herein the term "antigen" refers to any polypeptide or polypeptide fragment that will be used in the production of a antibodies. However it will be understood by one of skill in the art that in many cases antigens comprise more material that merely a single polypeptide. For example in certain aspects of the invention it is preferred that antibodies recognize AP. In certain other aspects of the invention antibodies will be generated against specific polypeptide antigens from *Francisella* such as a *Francisella*-associated AP protease. Thus one of skill it the art would easily be able to generate an antibody that binds to any particular AP polypeptide (or region thereof) or a *Francisella*-associated AP protease.

In the case where an antibody is to be generated that binds to a particular polypeptide it may be useful to conjugate the antigen or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, $SOCl_2$, or $R^1N=C=NR$, where R and $R^1$ are different alkyl groups.

Animals are immunized against the immunogenic conjugates or derivatives by combining 1 mg to 1 μg of conjugate (for rabbits or mice, respectively) with 3 volumes of Freud's complete adjuvant and injecting the solution intradermally at multiple sites. One month later the animals are boosted with ⅕ to ⅒ the original amount of conjugate in Freud's complete adjuvant by subcutaneous injection at multiple sites. 7 to 14 days later the animals are bled and the serum is assayed for specific antibody titer. Animals are boosted until the titer plateaus. Preferably, the animal boosted with the same antigen conjugate, but conjugated to a different protein and/or through a different cross-linking reagent. Conjugates also can be made in recombinant cell culture as protein fusions. Also, aggregating agents such as alum are used to enhance the immune response.

B. Monoclonal Antibodies

In preferred embodiments of the invention the cell targeting moiety is a monoclonal antibody. By using monoclonal a great specificity may be achieved. This may reduce the background in assays of the invention. Furthermore, monoclonal antibodies that bind to specific regions (epitopes) of an AP polypeptide any be ideal for assessing AP cleavage. Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, monoclonal antibodies of the invention may be made using the hybridoma method first described by Kohler & Milstein (1975), or may be made by recombinant DNA methods (Cabilly et al.; U.S. Pat. No. 4,816,567).

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding 1986).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA.

Culture medium in which hybridoma cells are growing is assayed for production of monoclonal antibodies directed against the target antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard (1980).

After hybridoma cells are identified that produce antibodies of the desired specificity, affinity, and/or activity, the clones may be subcloned by limiting dilution procedures and grown by standard methods, Goding (1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al. (1984), or by covalently joining to the immunoglobulin coding sequence all or part of the coding sequence for a non-immunoglobulin polypeptide. In that manner, "chimeric" or "hybrid" antibodies are prepared that have the binding specificity for any particular antigen described herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for the target antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; biotin; radioactive isotopic labels, such as, e.g., $^3H$, $^{14}C$, $^{32}P$, $^{35}S$, or $^{125}I$, or an enzyme, such as alkaline phosphatase, beta-galactosidase or horseradish peroxidase.

Any method known in the art for separately conjugating the antibody to the detectable moiety may be employed, including those methods described by Hunter et al. (1962); David et al. (1974); Pain et al. (1981); and Nygren (1982).

The antibodies of the present invention may be employed in any known assay method, such as competitive binding assays, direct and indirect sandwich assays, and immunoprecipitation assays (Zola, 1987).

Competitive binding assays rely on the ability of a labeled standard (which may be a purified target antigen or an immunologically reactive portion thereof) to compete with the test sample analyte for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected (e.g., AP). In a sandwich assay, the test sample analyte is bound by a first antibody which is immobilized on a solid support, and thereafter a second antibody binds to the analyte, thus forming an insoluble three part complex (see, U.S. Pat. No. 4,376,110). The second antibody may itself be labeled with a detectable moiety (direct sandwich assays) or may be measured using an anti-immunoglobulin antibody that is labeled with a detectable moiety (indirect sandwich assay). In aspects of the invention, such assays may be used to assess AP polypeptide cleavage. One type of sandwich assay is an ELISA assay, in which case the detectable moiety is an enzyme.

C. Humanized Antibodies

As discussed previously, antibodies for use in the methods of the invention may be polyclonal or monoclonal antibodies or fragments thereof. However, in some aspects it is preferred that the antibodies are humanized such that they do not elicit an immune response in subject being treated. This aspect is important for example when antibodies will be used as protease inhibitors to treat a *Francisella* infection. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., 1986); Riechmann et al., 1988; Verhoeyen et al., 1988), by substituting rodent CDRs or CDR sequences for the corresponding sequences of a human antibody. Accordingly, such "humanized" antibodies are chimeric antibodies, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties, for example the ability to be internalized into cells. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed Aug. 21, 1992, which is a continuation-in-part of application Ser. No. 07/715,272 filed Jun. 14, 1991.

D. Human Antibodies

Human monoclonal antibodies can be made by the hybridoma method. Human myeloma and mouse-human heteromyeloma cell lines for the production of human monoclonal antibodies have been described, for example, by Kozbor (1984) and Brodeur et al. (1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al. (1993); Jakobovits et al. (1993).

Alternatively, the phage display technology (McCafferty et al., 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle.

Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; see Winthrop et al., 2003 or for a review see, e.g. Johnson et al. (1993). Several sources of V-gene segments can be used for phage display. Clackson et al. (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al. (1991), or Griffith et al. (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This techniques allows the production of antibodies and antibody fragments with affinities in the nM range. A strategy for making very large phage antibody repertoires (also known as "the mother-of-all libraries") has been described by Waterhouse et al. (1993), and the isolation of a high affinity human antibody directly from such large phage library has been reported. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213). Unlike traditional humanization of rodent antibodies by CDR grafting, this technique provides completely human antibodies, which have no framework or CDR residues of rodent origin.

E. Single Chain Antibodies

Single chain antibodies (SCAs) are genetically engineered proteins designed to expand on the therapeutic and diagnostic applications possible with monoclonal antibodies. SCAs have the binding specificity and affinity of monoclonal antibodies and, in their native form, are about one-fifth to one-sixth of the size of a monoclonal antibody, typically giving them very short half-lives. Human SCAs offer many benefits compared to most monoclonal antibodies, including more specific localization to target sites in the body, faster clearance from the body, and a better opportunity to be used orally, intranasally, transdermally or by inhalation, for example. In addition to these benefits, fully-human SCAs can be isolated directly from human SCA libraries without the need for costly and time consuming "humanization" procedures. SCAs are also readily produced through intracellular expression (inside cells) allowing for their use in gene therapy applications where SCA molecules act as specific inhibitors of cell function.

Single-chain recombinant antibodies (scFvs) consist of the antibody VL and VH domains linked by a designed flexible peptide tether (Atwell et al., 1999). Compared to intact IfGs, scFvs have the advantages of smaller size and structural simplicity with comparable antigen-binding affinities, and they can be more stable than the analogous 2-chain Fab fragments (Colcher et al., 1998; Adams and Schier, 1999). Several studies have shown that the smaller size of scFvs provides better penetration into tumor tissue, improved pharmacokinetics, and a reduction in the immunogenicity observed with i.v. administered Fabs compared to that of intact murine antibodies (Bird et al., 1988; Cocher et al., 1990; Colcher et al., 1998; Adams and Schier, 1999).

The variable regions from the heavy and light chains (VH and VL) are both approximately 110 amino acids long. They can be linked by a 15 amino acid linker or longer with the sequence, for example, which has sufficient flexibility to allow the two domains to assemble a functional antigen binding pocket. In specific embodiments, addition of various signal sequences allows the scFv to be targeted to different organelles within the cell, or to be secreted. Addition of the light chain constant region (Ck) allows dimerization via disulfide bonds, giving increased stability and avidity. Thus, for a single chain Fv (scFv) SCA, although the two domains of the Fv fragment are coded for by separate genes, it has been proven possible to make a synthetic linker that enables them to be made as a single protein chain scFv (Bird et al., 1988; Huston et al., 1988) by recombinant methods. Furthermore, they are frequently used due to their ease of isolation from phage display libraries and their ability to recognize conserved antigens (for review, see Adams and Schier, 1999). For example, scFv is utilized to target suicide genes to carcinoembryonic antigen (CEA)-expressing tumor cells by a retrovector displaying anti-CEA scFv (Kuroki et al., 2000).

F. Bispecific Antibodies

Methods for making bispecific antibodies are known in the art. Traditionally, the recombinant production of bispecific antibodies is based on the coexpression of two immunoglobulin heavy chain-light chain pairs, where the two heavy chains have different specificities (Millstein and Cuello, 1983). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829, and in Traunecker et al. (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $CH_2$ and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in copending application Ser. No. 07/931,811 filed Aug. 17, 1992. For further details of generating bispecific antibodies see, for example, Suresh et al. (1986).

G. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

III. Polypeptide Purification

A polypeptide (e.g., AP polypeptide) may be isolated and/or purified from after chemical synthesis, or from tissues, cells or cellular components. Purification can be accomplished by any appropriate technique that is described in the specification or known to those of skill in the art (e.g., Sambrook et al., 1989). Although preferred for use in certain embodiments, there is no general requirement that polypeptide such as AP always be provided in their most purified state. Indeed, it is contemplated that a less substantially purified AP, which is nonetheless enriched in the desired compound, relative to the natural state, will have utility in certain embodiments. As described above purified AP such as CIP may also be obtained from a variety of commercial sources.

Some example techniques that may be used for polypeptide purification include but are not limited to, precipitation with ammonium sulfate, PEG, antibodies and the like or by heat denaturation, followed by centrifugation; fractionation, chromatographic procedures, including but not limited to, partition chromatograph (e.g., paper chromatograph, thin-layer chromatograph (TLC), gas-liquid chromatography and gel chromatography) gas chromatography, high performance liquid chromatography, affinity chromatography, supercritical flow chromatography, ion exchange chromatography, gel filtration chromatography, reverse phase chromatography, hydroxylapatite chromatography, lectin affinity chromatography; isoelectric focusing and gel electrophoresis (see for example, Sambrook et al. 1989; and Freifelder, Physical Biochemistry, Second Edition, pages 238-246).

IV. Immuno Detection

Thus, in certain aspects the present invention concerns immunodetection methods for binding, purifying, removing, quantifying and/or otherwise generally detecting biological components such as AP polypeptide components. The anti-AP antibodies prepared in accordance with the present invention may be employed to detect wild-type and/or mutant AP proteins, polypeptides and/or peptides and/or cleavage products thereof. As described throughout the present application, the use of wild-type and/or mutant AP specific antibodies is contemplated. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle MH and Ben-Zeev O, 1999; Gulbis B and Galand P, 1993; De Jager R et al., 1993; and Nakamura et al., 1987, each incorporated herein by reference.

In general, the immunobinding methods include obtaining or having a sample suspected of containing AP polypeptide and/or AP cleavage product, and contacting the sample with a first anti-AP antibody in accordance with the present invention, as the case may be, under conditions effective to allow the formation of immunocomplexes.

These methods include methods for purifying wild-type and/or mutant AP polypeptide and/or AP cleavage product as may be employed in purifying wild-type and/or mutant AP polypeptide and/or AP cleavage products from patients' samples. In these instances, the antibody removes the antigenic wild-type and/or mutant AP polypeptide and/or AP cleavage product from a sample. The antibody will preferably be linked to a solid support, such as in the form of a column matrix, and the sample suspected of containing the wild-type or mutant Ap polypeptide of AP cleavage product will be applied to the immobilized antibody. The unwanted components will be washed from the column or support, leaving the antigen immunocomplexed to the immobilized antibody, which wild-type or mutant AP protein antigen is then collected by removing the wild-type or mutant AP protein and/or peptide from the column.

The immunobinding methods also include methods for detecting and quantifying the amount of a wild-type or mutant AP polypeptide or AP cleavage product in a sample and the detection and quantification of any immune complexes formed during the binding process. Here, one would obtain a sample suspected of containing an AP polypeptide or AP degradation product (e.g., an AP cleavage product) and contact the sample with an antibody against a wild-type or mutant AP, and then detect and quantify the amount of immune complexes formed under the specific conditions. In terms of antigen detection, a biological sample analyzed may be any sample that is suspected of containing an AP polypeptide-specific antigen as described supra, such as a tissue section, blood, saliva or urine sample.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any AP antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277, 437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The anti-AP antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

The immunodetection methods of the present invention have evident utility in the diagnosis and prognosis of conditions such as various forms of *Francisella* infection. Here, a biological and/or clinical sample suspected of containing a an AP protein, polypeptide, peptide, mutant and/or cleavage product is used. However, these embodiments also have applications to non-clinical samples, such as in the titering of antigen or antibody samples, for example in the selection of hybridomas.

In the clinical diagnosis and/or monitoring of patients with a *Francisella* infection, the detection of AP cleavage, and/or an alteration in the levels of serum AP, in comparison to the levels in a corresponding biological sample from a normal subject is indicative of a patient with a *Francisella* infection. However, as is known to those of skill in the art, such a clinical diagnosis would not necessarily be made on the basis of this method in isolation. Those of skill in the art are very familiar with differentiating between significant differences in types and/or amounts of biomarkers, which represent a positive identification, and/or low level and/or background changes of biomarkers. Indeed, background expression levels are often used to form a "cut-off" above which increased detection will be scored as significant and/or positive.

A. ELISAS

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, flow cytometry analyses, and/or the like may also be used.

In one exemplary ELISA, the anti-AP antibodies of the invention are immobilized onto a selected surface exhibiting protein affinity, such as a well in a polystyrene microtiter plate. Then, a test composition suspected of containing AP polypeptides and/or cleavage products thereof, such as a clinical sample, is added to the wells. After binding and/or washing to remove non-specifically bound immune complexes, the bound AP antigen may be detected. Detection is generally achieved by the addition of another anti-AP antibody that is linked to a detectable label. This type of ELISA is a simple "sandwich ELISA". Detection may also be achieved by the addition of a second anti-AP antibody, followed by the addition of a third antibody that has binding affinity for the second antibody, with the third antibody being linked to a detectable label.

In another exemplary ELISA, the samples suspected of containing an AP antigen are immobilized onto the well surface and/or then contacted with the anti-AP antibodies of the invention. After binding and/or washing to remove non-specifically bound immune complexes, the bound anti-AP antibodies are detected. Where the initial anti-AP antibodies are linked to a detectable label, the immune complexes may be detected directly. Again, the immune complexes may be detected using a second antibody that has binding affinity for the first anti-AP antibody, with the second antibody being linked to a detectable label.

Another ELISA in which the AP antigens are immobilized, involves the use of antibody competition in the detection. In this ELISA, labeled antibodies against AP are added to the wells, allowed to bind, and/or detected by means of their label. The amount of AP antigen or cleavage product in an unknown sample is then determined by mixing the sample with the labeled antibodies against AP before and/or during incubation with coated wells. The presence of AP polypeptide in the sample acts to reduce the amount of antibody against AP available for binding to the well and thus reduces the ultimate signal. This is also appropriate for detecting anti-AP antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/TWEEN (polysorbate). These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C.

Following all incubation steps in an ELISA, the contacted surface is washed so as to remove non-complexed material. A preferred washing procedure includes washing with a solution such as PBS/TWEEN (polysorbate), or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-TWEEN (polysorbate)).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

B. Immunohistochemistry

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

C. Immunoelectron Microscopy

The antibodies of the present invention may also be used in conjunction with electron microscopy to identify intracellular tissue components. Briefly, and electron-dense label is conjugated directly or indirectly to the anti-AP antibody. Examples of electron-dense labels according to the invention are ferritin and gold. The electron-dense label absorbs electrons and can be visualized by the electron microscope.

D. Antibody Conjugates

The present invention further provides antibodies against AP proteins, polypeptides and peptides, generally of the monoclonal type, that are linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled molecules, antiviral agents, chelating agents, cytokines, growth factors, and oligo- or poly-nucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotypes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody-directed imaging".

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III)

and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$-carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, CASCADE BLUE (8-hydroxypyrene-1,3,6-trisulfonic acid), Cy3, Cy5,6-FAM, Fluorescein Isothiocyanate, HEX, 6-JOE, OREGON GREEN 488 (2',7'-difluorofluorescein), OREGON GREEN 500 (2-(6-hydroxy-3-oxo-9,9a-dihydro-3H-xanthen-9-yl)benzenesulfonic acid), OREGON GREEN 514 (2',4,5,7,7'-pentafluorofluorescein), Pacific Blue, REG, Rhodamine Green, Rhodamine Red, Renographin, ROX, TAMRA, TET, Tetramethylrhodamine, and/or TEXAS RED (sulforhodamine 101 acid chloride).

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase, luciferase (e.g., renilla or firefly luciferase) or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

In another embodiment of the invention, the anti-AP antibodies are linked to semiconductor nanocrystals such as those described in U.S. Pat. Nos. 6,048,616; 5,990,479; 5,690,807; 5,505,928; 5,262,357 (all of which are incorporated herein in their entireties); as well as PCT Publication No. 99/26299 (published May 27, 1999). In particular, exemplary materials for use as semiconductor nanocrystals in the biological and chemical assays of the present invention include, but are not limited to those described above, including group II-VI, III-V and group IV semiconductors such as ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, PbS, PbSe, Ge and Si and ternary and quaternary mixtures thereof. Methods for linking semiconductor nanocrystals to antibodies are described in U.S. Pat. Nos. 6,630,307 and 6,274,323.

V. Kits

In still further embodiments, the present invention concerns kits for use in detection of *Francisella* bacteria or *Francisella*-associated AP protease activity in a sample. For example, such kits may provide AP binding antibodies in a ready to use assay system for detecting AP cleavage in a sample. Furthermore, kits may comprise AP polypeptide and a ready to use assay system for detecting the cleavage thereof. As described above such an assay system may detect A cleavage via a change in signal from a label associated with the provided AP or by detecting a loss in AP enzymatic activity.

The container of the kits can generally include at least one vial, test tube, flask, bottle, syringe and/or other container, into which at least one AP-binding antibody, labeled AP polypeptide or antibody that binds to a *Francisella*-associated AP protease may be placed, and/or preferably, suitably aliquoted. The kits of the present invention may include a means for containing the assay system or any other reagent containers in close confinement for commercial sale. Such containers may include injection and/or blow-molded plastic containers into which the desired vials are retained. Furthermore, such kits may comprise a suitable instruction manual and tables or diagrams to aid in performing assays according to the invention.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Experimental Procedures

Bacterial Strains

The following strains of *Francisella tularensis* species and subspecies were used: *F. novicida* (U112 strain); *F. tularensis* LVS (Lot #16); *F. tularensis* subsp. *tularensis* (type A) (Schu S4 strain); and *F. tularensis* subsp. *holarctica* (type B) (OR96-0246 strain). *Klebsiella pneumoniae* (KPPR1 strain) (Lawlor et al., 2005) and *Salmonella typhimurium* (UK-1 strain) (Zhang et al., 1999) were used as specificity controls. Bacteria were grown at 37° C. in Trypticase Soy Broth (TSB) or on Trypticase Soy Agar (TSA), each supplemented with 0.1% cysteine, for 24-48 h (Lauriano et al., 2004; Pammit et al., 2004; Pammit et al., 2006). Aliquots of bacterial stock cultures were frozen at −80° C. in TSB containing 0.1% cysteine and 30% glycerol.

Mice

Five-to eight-week old, female, BALB/c mice and C57BL/6 mice were obtained from the Jackson Laboratory (Bar Harbor, Me.). All animal care and experimental procedures were performed in compliance with the Institutional Animal Care and Use Committee guidelines.

Intranasal (i.n.) Challenge and Bacteremia Assessment

For in vivo challenges, mice were first anesthetized with 3% isoflurane using a rodent anesthesia system (Harvard Apparatus, Holliston, Mass.) and then inoculated i.n. with 100 colony forming units (CFU) of either *F. tularensis* type A ($LD_{50}$ of 1 CFU) or *F. tularensis* type B ($LD_{50}$ of 10 CFU), or with 400 CFU of *F. novicida* ($LD_{50}$ of 10 CFU), *F. tularensis* LVS ($LD_{50}$ of 1800 CFU), *K. pneumoniae* ($LD_{50}$ of $5 \times 10^3$ CFU) (Lawlor et al., 2005), or *S. typhimurium* ($LD_{50}$ of $9 \times 10^3$ CFU) (Zhang et al., 1999), in 25 µl of phosphate buffered saline (PBS). The concentrations of the bacterial inocula for each experiment were determined by serial dilution and plating on TSA. Colonies were enumerated after 24-36 h of incubation at 37° C. Mice were weighed and monitored daily for morbidity and mortality. Bacteremia was assessed in groups of infected animals by removal of target organs at various intervals (24 h, 48 h, and 72 h) post challenge. Organs were homogenized using an electric homogenizer (Arrow Junior; Kimble/Kontes, Vineland, N.J.). Homogenates were serially diluted and plated on TSA for bacterial enumeration, as previously described (for example see, Pammit et al. (2004) or Pammit et al. (2006)).

Preparation of Cell-Free Plasma

Mice were bled at 24 h, 48 h, and 72 h after i.n. challenge, and plasma was prepared using plasma collection tubes containing lithium and heparin sulfate (Fisher Scientific, NJ). The samples were centrifuged for 5 min at 5000 rpm, and the plasma was plated on TSA for bacterial enumeration or frozen at −20° C. Additionally, cytospins were prepared with the infected plasma and stained using an anti-Francisella LPS #8.2 monoclonal antibody, conjugated to Alexa 488 (BD Bioscience, San Jose, Calif.) (Pammit et al., 2006). For adoptive transfer studies, naïve animals were injected intraperitoneally (i.p.) with 200 µl of either *F. novicida*-infected or mock-infected plasma. All animals were weighed daily and monitored for morbidity and mortality.

In-Vivo Plasma Biochemical Assays

Albumin content, as well as alanine aminotransferase (ALT), aspartate aminotransferase (AST), and alkaline phosphatase (AP) activity levels in naïve and infected plasma were measured at the University of Texas Health Science Center at San Antonio using an Olympus AU640e Chemistry Immuno Analyzer (Olympus, Center Valley, Pa.). Plasma from infected mice also was analyzed for AP activity (nmoles or pmoles/min/µl) in 96 well microplates by measuring the rate of hydrolysis of 4-paranitrophenyl phosphate (PNPP) (Sigma-Aldrich, St. Louis, Mo.) or 4-methylumbelliferyl phosphate (4-MUP) (Sigma-Aldrich), as previously described (Voller et al., 1976; Fernley & Walker, 1969). Briefly, plasma samples (10 µl) were added to 190 µl of a substrate solution containing 1.9 mM PNPP dissolved in AP buffer (0.1 M glycine-1 mM $MgCl_2$-1 mM $ZnCl_2$ buffer, pH 10.4). Microplates were incubated at 37° C., and substrate hydrolysis was monitored spectrophotometrically at 410 nm every 10 min for 1 h using an uQuant Microplate Spectrophotometer (Biotek, Winooski, Vt.). For fluorometric analyses, 10 µl of a 1:10 dilution of plasma and AP buffer were added to 190 µl of a substrate solution containing 0.5 mM 4-MUP dissolved in AP buffer. Microplates were incubated at 37° C. with moderate shaking, and the hydrolysis of substrate was monitored fluorometrically at 360 nm (excitation) and 465 nm (emission) every 10 min for 1 h using a Synergy HT Multidetection Plate Reader (Biotek). Quantification of substrate hydrolysis was determined using either a linear paranitrophenol (PNP) standard curve (0-60 nmoles) or a linear 4-methylumbelliferone (4-MU) standard curve (0-6 pmoles) generated under identical assay conditions, in the absence of PNPP or 4-MUP, respectively.

In-Vitro Plasma and Calf-Intestinal Alkaline Phosphatase (CIP) AP Assays

Plasma (180 µl) from naive mice was combined separately with 20 µl of each of the following: TSB containing $1 \times 10^6$ CFU of either live, heat killed, or sonicated *F. novicida*, *F. tularensis* LVS, or *K. pneumoniae*, TSB containing 10-20 µg of *F. novicida*, *F. tularensis* LVS, or *E. coli* lipopolysaccharide (LPS) (Sigma-Aldrich), or TSB alone. All samples were incubated at 37° C. with gentle shaking for 24 h and 48 h. The samples were subsequently centrifuged, and the plasma was analyzed fluorometrically for AP activity, as previously described. The AP activity (pmoles/min/µl) of each infected sample was divided by the AP activity of the mock samples, subtracted from 1, and normalized to 100 to determine the % AP inhibition. To directly assess the inhibitory effect of *F. tularensis* on AP activity, known concentrations of CIP (New England Laboratories, Ipswich, Mass.) were combined with *Francisella* in the presence of lipase (Sigma-Aldrich), β-glucosidase (Sigma-Aldrich), or an EDTA-Free Protease Inhibitor Cocktail (Roche Diagnostics, Germany). The CIP was diluted in sterile saline to a concentration of 0.001 units/μl and was combined separately with TSB containing $1 \times 10^6$ CFU of *F. novicida*, plus either 0.2-0.5 μg of protease inhibitor, or 2-20 units of β-glucosidase or lipase. All samples were incubated at 37° C. with gentle shaking for 24 h and 48 h. The samples were centrifuged, and the supernatants were analyzed fluorometrically for AP activity, as previously described. All inocula were serially diluted and plated on TSA for bacterial enumeration.

SDS-PAGE and Detection of AP by Zymogram and Western Blot Analyses

Plasma samples from naïve or infected mice, or aliquots of CIP incubated with or without *Francisella*, were characterized using SDS-PAGE. For zymogram analyses, gels were rinsed 3× with AP buffer and incubated at 37° C. with gentle shaking for 10-15 min in 20 ml of a substrate buffer, consisting of 5 mM 4-MUP dissolved in AP buffer. AP activity was detected by exposure of the gel to ultraviolet light, and the observed bands were photographed using a Polaroid Photo-Documentation Camera (Fisher). For Western blot analyses, proteins were first transferred from gels to a PVDF membrane (BioRad, Hercules, Calif.) and then blocked overnight at 4° C. with 5% skim milk in PBS. The membranes were gently rocked and incubated for 2 h at 25° C. with the anti-mouse AP antibodies PLAP-H300 (Santa Cruz Biotechnology, Santa Cruz, Calif.) for detection of all AP isoforms, or TNAP-N18 (Santa Cruz Biotechnology), for detection of the liver AP isoform. All membranes were then rinsed 3× with 0.1% Tween-20 (Sigma), dissolved in PBS (PBST), and incubated with detecting antibodies for 1 h (with gentle rocking) at 25° C. The blots were developed using the ECL Western Blotting Detection Reagent System (GE Healthcare-Life Sciences Division, Piscataway, N.J.) and imaged.

Histology

Mice were sacrificed at timed intervals following i.n. challenge with *F. novicida* or *F. tularensis* LVS, and livers were harvested from the perfused animals. Tissues were embedded in optimal cutting temperature (OCT) resin and snap frozen. Serial cryosections were prepared and placed on silane coated slides (VWR International, West Chester, Pa.). Slides were dried overnight, fixed with methanol, and stained with hematoxylin and eosin (H&E) (Pammit et al., 2006). Representative photomicrographs were acquired using an Axiocam digital camera (Zeiss, Thornwood, N.Y.) connected to an Axioskop 2 Plus research microscope (Zeiss). Neutrophils were identified using a rat anti-mouse Ly-6G (GR-1) monoclonal antibody (BD Biosciences), followed by staining with anti-rat Ig conjugated with horseradish peroxidase (HRP), according to the manufacturer's instructions (BD Bioscience). Sections were imaged at 40× and 100× magnification.

Phagocytosis and AP Production in Primary Hepatocytes

For in vitro cultures, perfused livers were harvested from naïve mice, collaganease/DNase digested (1.4 μg/ml), and single cell suspensions were prepared in phenol red free Dulbecco's Modified Eagle's Medium (Cellgro, Herndon, Va.), supplemented with 10% heat inactivated fetal bovine serum (FBS). Primary liver cells ($5 \times 10^5$ cells/well) were seeded and infected with *F. novicida* or *F. tularensis* LVS, at a multiplicity of infection (MOI) of 10:1 or 100:1, for 2 h at 37° C. Cultures were then treated for an additional 1 h with medium containing gentamicin (10 μg/ml) (Sigma-Aldrich) to eliminate extracellular bacteria and subsequently cultured for 24 h in medium alone. Following incubation, the cells were lysed in 0.2% deoxycholic acid sodium salt (Sigma), and prepared lysates were serially plated on TSA to allow for enumeration of viable bacteria (Pammit et al., 2004). Cell lysates and supernatants also were analyzed fluorometrically for AP activity, as described previously.

Statistical Analyses

Survival data were analyzed by the Kaplan-Meier test, and all other data were evaluated by the Student's t test using the SigmaStat statistical software program. The data are presented as mean values±standard deviation. The number of repetitions of each study is indicated in the figure legends. Each study was repeated at least twice.

Example 2

Dissemination of *Francisella* Upon Intranasal Challenge

Figure 1A:
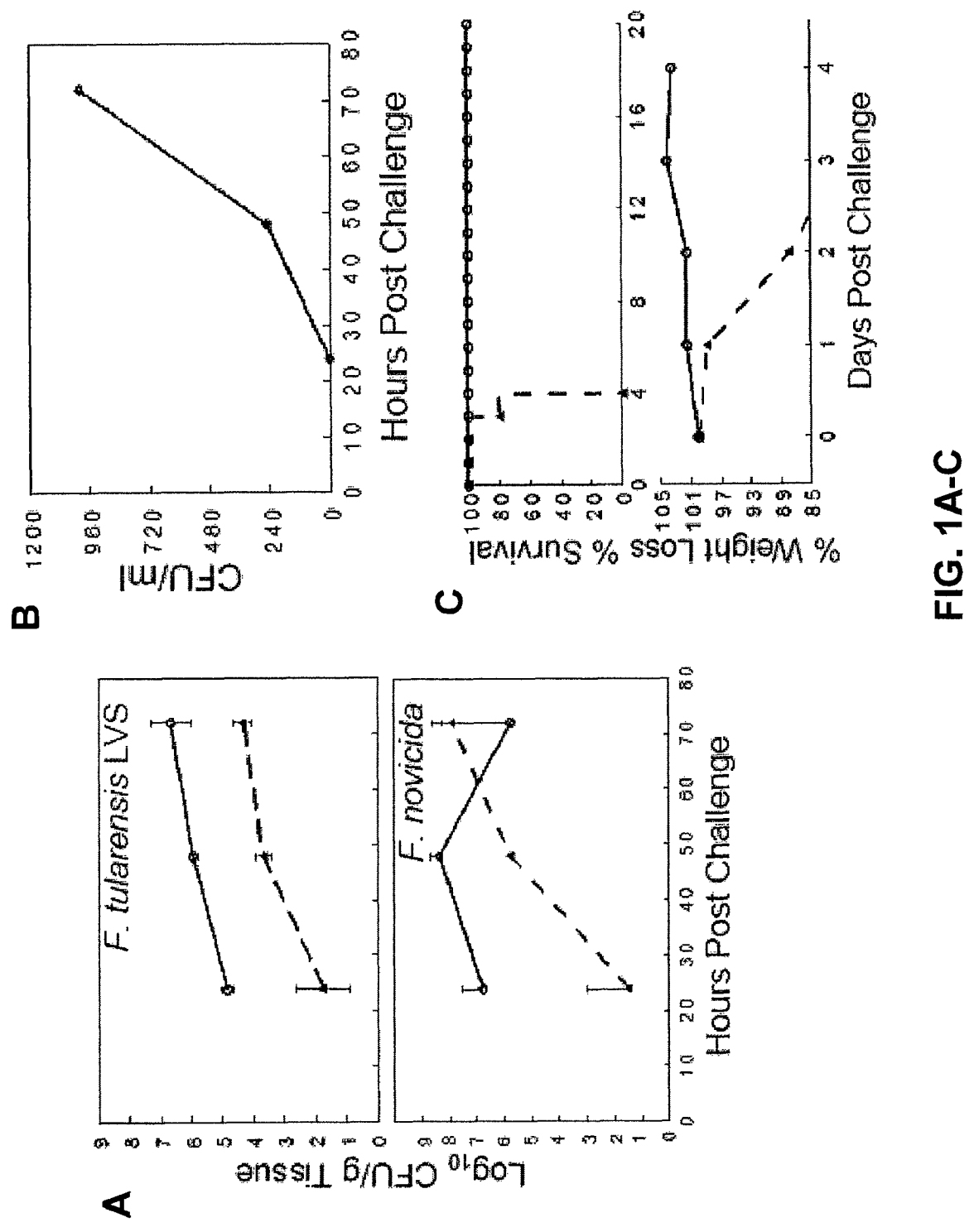

Bacterial load in the lungs and livers of *F. tularensis* LVS or *F. novicida* infected animals was assessed by plating tissue homogenates. Within 24 h of pulmonary challenge with 400 colony forming units (CFU) of *F. tularensis* LVS, a significant number of bacteria, $1 \times 10^4$ CFU/g tissue, was observed in the lungs, which increased to $1 \times 10^6$ CFU/g tissue by 72 h. Livers of infected animals exhibited a near 300-fold increase in recoverable bacteria during the same monitoring period, rising from 100 CFU/g tissue at 24 h to $1 \times 10^4$ CFU/g tissue by 72 h. In comparison, lungs from *F. novicida* (400 CFU) challenged mice demonstrated a higher initial number of viable organisms, with a recovery of $1 \times 10^7$ CFU/g tissue at 24 h, which gradually decreased to $1 \times 10^6$ CFU/g tissue by 72 h. There was a progressive increase in the bacterial load of livers from *F. novicida* infected mice, with levels rising from 100 CFU/g tissue at 24 h to $1 \times 10^7$ CFU/g tissue by 72 h (FIG. 1A). These results demonstrate a temporal spread of bacteria from the lungs to the secondary organs after pulmonary exposure. To determine a probable mechanism for the rapidity of bacterial dissemination to the secondary organs, animals were bled at corresponding intervals following bacterial challenge, and cell-free plasma was prepared and plated to measure bacterial load. These analyses revealed that viable bacteria in circulation increased markedly over time, with minimal detection of bacteria at 24 h to nearly $1 \times 10^3$ CFU/ml by 72 h post challenge (FIG. 1B). The presence of bacteria in cell-free plasma was visualized further by immunofluorescent staining using an anti-LPS monoclonal antibody to confirm the presence of bacteria in the plasma. To demonstrate the highly infectious nature of this plasma, naïve mice were injected intraperitoneally (i.p) with plasma from either *F. novicida* or mock challenged animals. All mice were then weighed daily, and monitored for morbidity and mortality. Mice receiving plasma from *F. novicida* infected animals experienced significant reductions in body weight (25%) and died within 4 days of adoptive transfer, while mice receiving plasma from mock-challenged animals showed no outward signs of disease (FIG. 1C). These results indicate that, apart from intracellular translocation within phagocytic cells, *Francisella* also may actively disseminate in an extracellular phase to rapidly seed the secondary organs after pulmonary challenge.

Example 3

Pulmonary *Francisella* Infection Inhibits Plasma AP Activity

Because of the high degree of bacterial burden in the liver, we profiled a panel of enzymes in the plasma indicative of acute hepatic injury. As shown in FIG. 2, the activity levels of alanine aminotransferase (ALT) and aspartate aminotransferase (AST) were elevated 5-fold and 4-fold by 72 h compared to mock infected mice, consistent with the observations made by Chen et al. (2004). Levels of albumin remained constant in the plasma from both *Francisella* infected groups through 72 h post challenge. In contrast, there was a marked decrease in the activity levels of AP as early as 48 h after pulmonary challenge. Total AP activity was reduced from 200 IU/l at 24 h to 50 IU/l by 72 h post challenge, in plasma obtained from both *F. novicida* and *F. tularensis* LVS challenged animals (FIG. 2A,B). To determine if the inhibitory effect of AP was specific to *Francisella*, we examined plasma from animals challenged i.n. with two other model Gram negative organisms, *K. pneumoniae* and *S. typhimurium*. As shown in FIG. 3A-B, AP activity in the plasma was relatively unchanged upon infection with either *K. pneumoniae* or *S. typhimurium*. In contrast, as previously observed, there was a marked reduction of AP activity (70% by 72 h) in plasma from both *F. tularensis* LVS and *F. novicida* challenged mice. These results suggest that the inhibitory effects on host AP activity may be specific to *Francisella* genus.

Example 4

Reduced AP Activity Correlates with AP Protein Degradation in Plasma from *Francisella* Infected Mice Zymogram and Western blot analyses were performed to correlate the reduction of AP activity with the degradation of the AP protein in plasma from *F. tularensis* LVS or *F. novicida* (400 CFU) challenged animals. The zymograms, performed using 4-MUP, revealed the rapid inhibition of AP activity in plasma from *F. novicida* and *F. tularensis* LVS infected animals, with noticeable marked decreases by 72 h post challenge (FIG. 4A). In contrast, no reduction of AP activity was observed in plasma from *K. pneumoniae* infected animals. Western blot analyses of *Francisella* infected plasma, probed with an anti-mouse AP (PLAP-H300) antibody, revealed the expression of AP and concurrent detection of degraded secondary products (i.e., appearance of fragments) as early as 48 h after challenge. The appearance of degraded AP products was not seen in plasma from mice infected with *Klebsiella* at any time point (FIG. 4B). As previously observed, the AP activity in plasma from *F. novicida* and *F. tularensis* LVS infected mice was reduced by 70% at 72 h, whereas no inhibition of AP activity was observed in any of the *Klebsiella* infected plasma samples (FIG. 4C).

Similar zymogram analyses of animals infected with 100 CFU of the highly virulent *F. tularensis* type A or type B subspecies revealed significant reductions of AP activity by 48 h, which were further reduced by 72 h post challenge (FIG. 5A). Additionally, as observed with *F. tularensis* LVS and *F. novicida*, Western blot analyses revealed the expression and appearance of degraded secondary AP products by 48 h, in plasma from both type A and type B *F. tularensis* infected animals (FIG. 5B). Plasma from animals challenged with 100 CFU of *F. tularensis* type A exhibited a 67% reduction in AP activity, falling from 0.2 nmoles/min/μl to 0.05 nmoles/min/μl, while AP activity in *F. tularensis* type B infected plasma was reduced by 48%, dropping from 0.2 nmoles/min/μl to 0.1 mmoles/min/μl, by 72 h post challenge (FIG. 5C). These results indicate that the inhibitory effect of AP activity in plasma is seen with all the major species and subspecies of *Francisella* and results in the rapid degradation of this host protein following pulmonary exposure.

Example 5

Hepatic Pathology Associated with *F. tularensis* Pulmonary Challenge

Since the liver is a major source of AP production and a primary site for *F. tularensis* replication, we analyzed the temporal pathological changes that occur in the liver upon pulmonary *F. tularensis* infection. H&E analysis of liver sections from *F. tularensis* LVS (400 CFU) infected animals revealed minimal evidence of pathology 24 h after pulmonary challenge. However, by 48 h post challenge, there were signs of early necrotic lesions spaced evenly throughout the liver, and by 72 h, the necrotic lesions were more apparent and consolidated. The pathology observed in the liver after *F. novicida* challenge (400 CFU) was similar to that seen with *F. tularensis* LVS infection. However, the observed pathology developed sooner and displayed greater severity. Specifically, in *F. novicida* infected livers, small foci of inflammatory infiltrates, composed primarily of macrophages and neutrophils, were visualized as early as 24 h post challenge. By 48 h, the necrotic lesions were well defined, and by 72 h, multifocal inflammatory necrosis was apparent throughout the liver. Additionally, the presence of neutrophils within the necrotic lesions was confirmed by the appearance of polymorphic nuclei and staining with a rat anti-mouse Ly-6G (GR-1) monoclonal antibody. The influx of neutrophils was apparent by 48 h after challenge in both *F. novicida* and *F. tularensis* LVS infected liver sections. However, the degree of neutrophil involvement by 72 h after challenge was more severe in *F. novicida* infected livers than that seen in the *F. tularensis* LVS infected sections. The histopathological changes in the liver following pulmonary *F. tularensis* challenge correlated with the degree of bacterial burden and the concurrent reduction of plasma AP activity.

Example 6

Figure 7A:
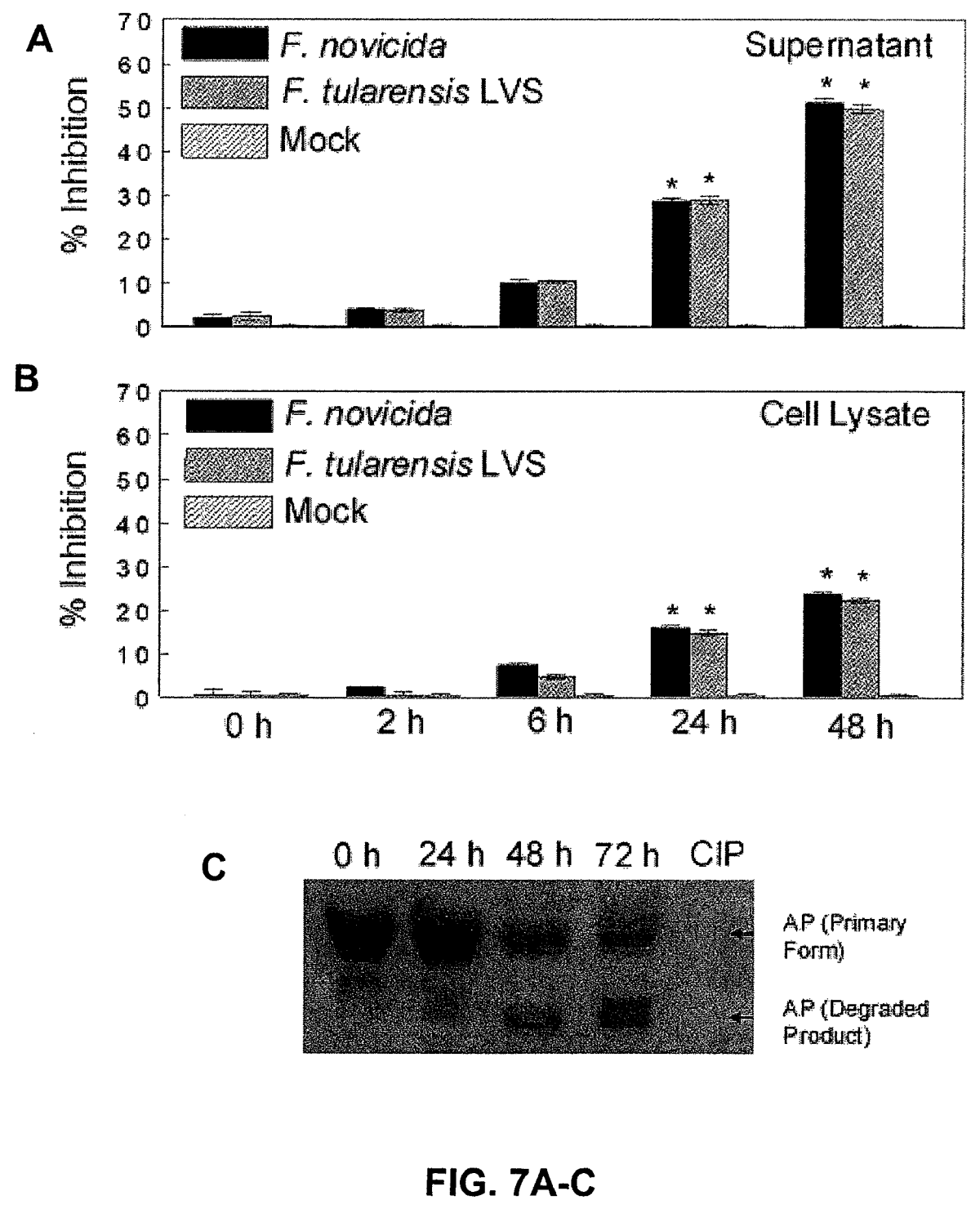

*F. tularensis* Replicates within Primary Mouse Hepatocytes and Inhibits Hepatic AP Activity To determine the role of the liver in the observed reduction of AP activity following pulmonary *F. tularensis* challenge, primary hepatocytes were prepared from naïve mice, exposed to either *F. novicida* or *F. tularensis* LVS (MOI 10:1 and 100:1) for 2 h, and treated with medium containing gentamicin for an additional 1 h. Hepatocytes were subsequently lysed and plated to determine bacterial replication. These analyses revealed that the numbers of *F. novicida* increased from 150 CFU/well at 3 h to $1 \times 10^5$ CFU/well by 24 h (MOI 10:1), and from 400 CFU/well at 3 h to $5 \times 10^5$ CFU/well by 24 h (MOI 100:1). Likewise, the concentrations of *F. tularensis* LVS increased from $1 \times 10^2$ CFU/well at 1 h to $1 \times 10^5$ CFU/well by 24 h (MOI 10:1), and from $1 \times 10^2$ CFU/well at 1 h to $2 \times 10^5$ CFU/well by 24 h (MOI 100:1) (FIG. 6). Additionally, the supernatants and cell lysates from infected hepatocytes were analyzed fluorometrically for AP activity. Supernatants from *F. novicida* and *F. tularensis* LVS cultures exhibited a 50% inhibition of AP activity by 48 h post challenge, whereas cell lysates revealed a 25% inhibition of AP activity by 48 h post challenge, when compared to mock infected hepatocytes (FIG. 7A, B).

To determine the isoform of AP affected by *F. tularensis* exposure, Western blot analyses of *F. novicida* infected plasma were carried out using an anti-mouse AP (TNAP-N18) antibody, which primarily detects, the liver isoform of AP. These analyses demonstrated an inhibition of AP expression by 48 h post challenge, with the concurrent detection of secondary AP fragments. The specificity of the TNAP-N18 antibody for the liver isoform of AP was evidenced by its inability to detect CIP (FIG. 8B). These results demonstrate the extreme susceptibility of hepatocytes to the *Francisella* infection, the marked decrease of AP activity within these cells, and the noticeable inhibition of the liver isoform of AP in plasma.

Example 7

Figure 8A:
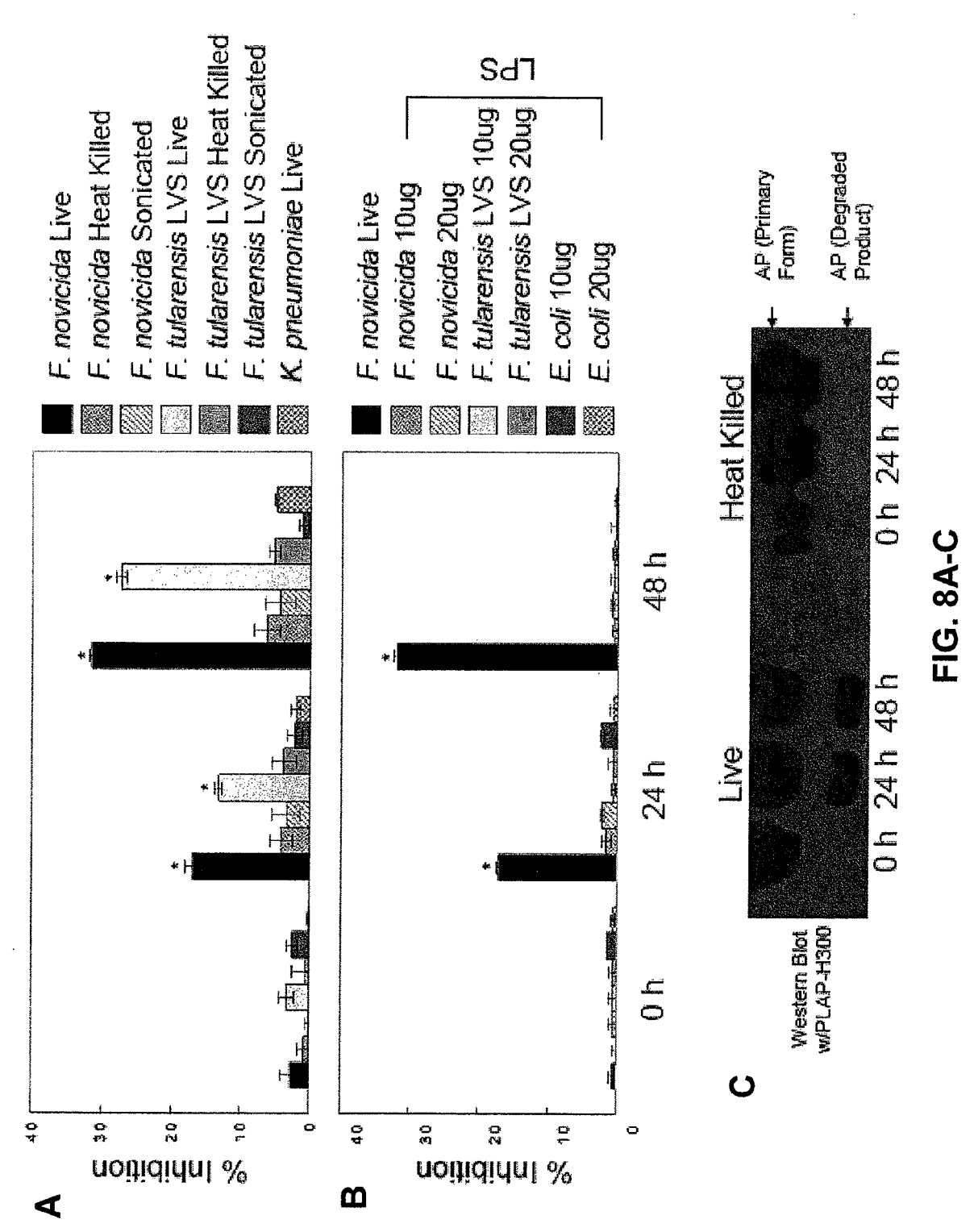

The Inhibition of AP Activity by *F. tularensis* Requires Live Replicating Organisms To determine if the inhibitory effect of AP requires live bacteria, and to evaluate the influence of *Francisella* lipopolysaccharide (LPS) in this process, an in-vitro assay was developed to measure AP activity. Normal plasma was combined individually with $1\times10^6$ CFU of live, heat-killed, or sonicated *F. novicida* or *F. tularensis* LVS, $1\times10^6$ CFU of live *K. pneumoniae*, or 10-20 µg of either *F. novicida*, *F. tularensis* LVS or *E. coli* LPS. The samples were incubated at 37° C. for 24 h and 48 h with gentle rocking and analyzed fluorometrically for AP activity. These analyses revealed a 28-30% inhibition of AP activity in plasma incubated with either live *F. tularensis* LVS or *F. novicida*. In contrast, plasma incubated with heat-killed or sonicated *F. novicida* or *F. tularensis* LVS, live *K. pneumoniae*, or *Francisella* or *E. coli* LPS exhibited only negligible amounts (up to 5%) of AP inhibition (FIG. 8A-B). Furthermore, Western blot analyses of normal plasma incubated with live *F. novicida*, performed using the PLAP H300 antibody, revealed the characteristic *Francisella*-induced, fragmented form of AP (FIG. 8C). In contrast, the appearance of this AP fragment was not observed in normal plasma incubated with heat killed *F. novicida*. These results suggest that *F. tularensis*-induced inhibition of AP activity requires replicating organisms and may suggest the need for synthesis and/or secretion of novel virulence factor(s).

Example 8

The Effect of *F. tularensis* on AP Activity is Dependent Upon the Generation of Bacterial Protease(s)

To ascertain the biochemical nature of *Francisella*-induced AP inhibition, a known concentration of CIP (0.001 units/µl) was incubated for 48 h at 37° C. with $1\times10^6$ CFU of *F. novicida*, or equivalent numbers of bacteria plus varying concentrations of protease inhibitor, lipase, or β-glucosidase. The incubated samples were analyzed fluorometrically for AP activity. These analyses revealed that the ability of *F. novicida* to inhibit CIP AP activity was markedly reduced in a dose dependent fashion by up to 93% in the presence of protease inhibitor, when compared to CIP incubated in the absence of protease inhibitor (FIG. 9A). As expected, CIP alone, or CIP in the presence of protease inhibitor, exhibited no reduction in AP activity. Additionally, the appearance of the degraded form of CIP AP was significantly abrogated in the presence of the protease inhibitor (FIG. 9B). In contrast, β-glucosidase and lipase treatment of CIP, incubated with *F. novicida*, had little effect on inhibition of AP activity (FIG. 9C, D). Taken together, these results indicate that active bacterial replication is required for the production of protease(s) which degrade and inhibit the activity of host AP.

Example 9

AP Activity Levels are Nominal in Vaccinated/Protected Animals

Figure 10A:
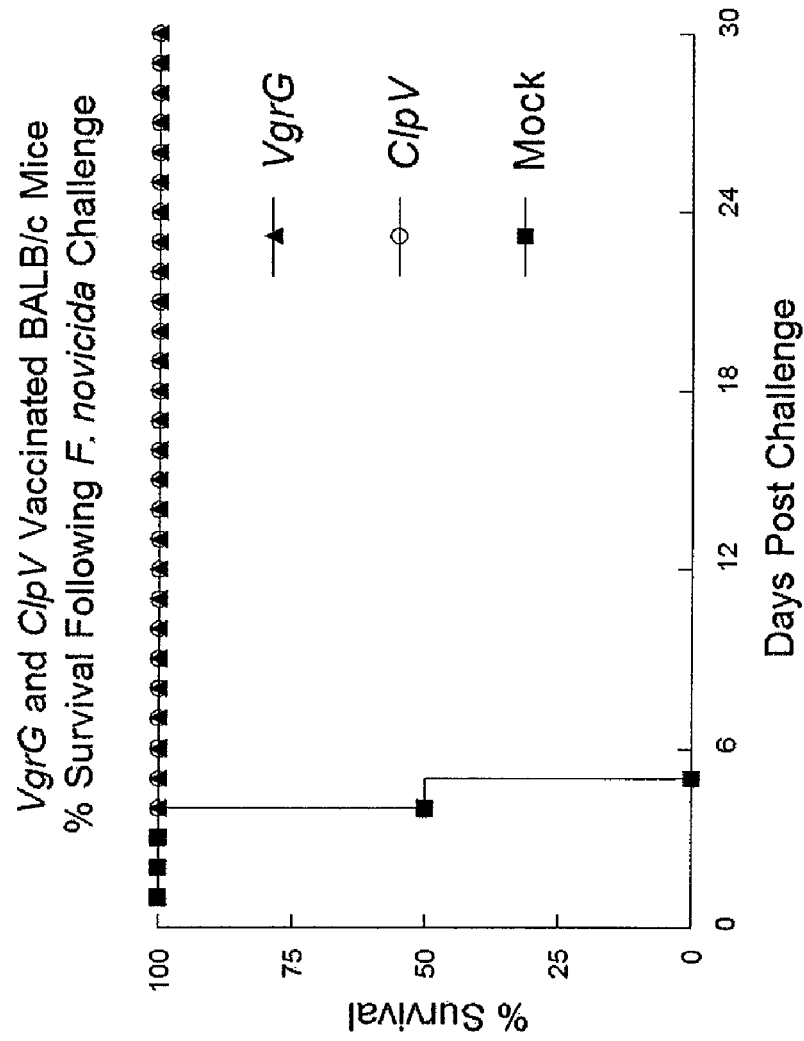
FIG. 10A-B: AP activity following challenge of vaccinated animals. Mice were intranasally vaccinated with either Clp V or VgrG attenuated mutant *Francisella novicida*, or mock immunized. Mice were then challenged with wild-type *F. novicida*.
Figure 10B:
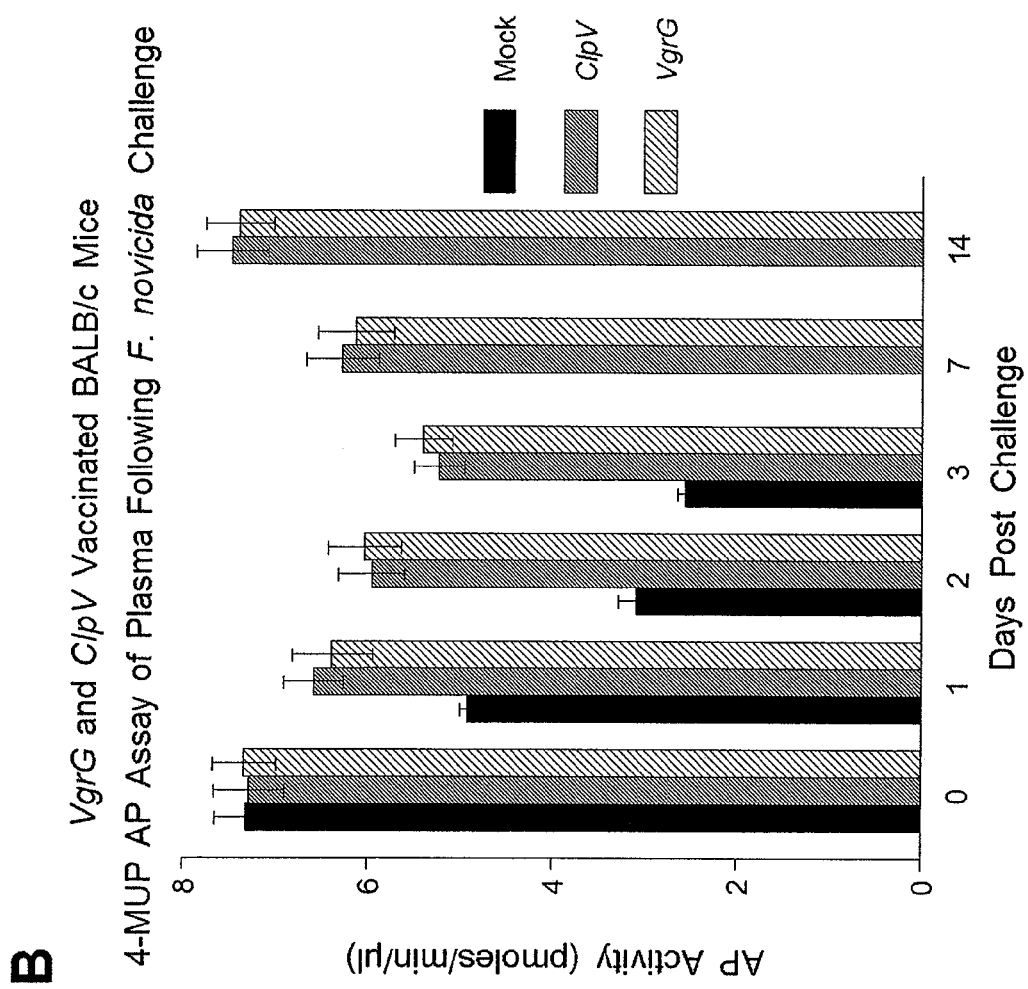

Five week-old female BALB/c mice (6 per group), were intranasally (i.n.) vaccinated with $1\times10^6$ CFU of either ClpV or VgrG mutants of *Francisella* novicida (defined attenuated strains), or mock immunized with PBS (Barker & Klose 2007). On day 30 post-immunization, all mice were challenged with $1.3\times10^3$ CFU (100 $LD_{50}$) of wild-type *F. novicida*. The mice were weighed daily and monitored for morbidity and mortality (FIG. 10A). For AP assays, plasma samples were collected from each animal one day before challenge with *F. novicida* (0 hr), and following challenge at 24 hr, 48 hr and 72 hr. Additionally, plasma was collected from all surviving immunized mice on day 7 and 14 post-challenge with *F. novicida*. The plasma AP activity was analyzed fluorometrically by measuring the rate of hydrolysis of the substrate 4-MUP, and compared to a standard curve generated with known concentrations of 4-MU (FIG. 10B).

Example 10

Figure 11:
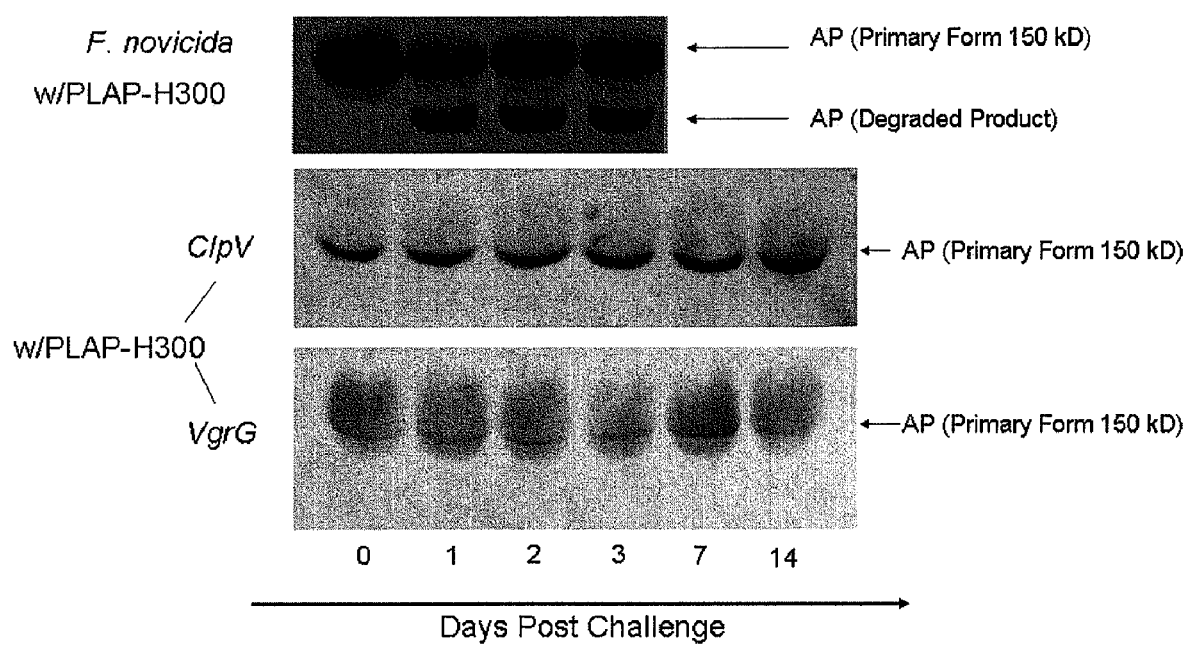
FIG. 11: AP activity in mice following pulmonary challenge with *F. novicida* or the defined secretion mutants of *F. novicida*, ClpV or VgrG. See Example 10 for details.

AP Activity Levels in Animals Challenged with *F. novicida* or Secretion Mutants Results of measuring AP activity in BALB/c mice following pulmonary challenge with *F. novicida* or the defined secretion mutants of *F. novicida*, ClpV or VgrG are shown in FIG. 11. Mice were bled at corresponding intervals and plasma prepared. As shown in FIG. 11, mice challenged with the wild-type novicida strain exhibit a marked reduction of AP activity in the plasma after 1 day following infection by the degradation and appearance of a $2^{nd}$ product by Western blot analyses using the PLAP-H300 detecting antibody (FIG. 11, top panel). In contrast, mice challenged with the secretion mutants did not show any appearance of degradation of AP activity in the plasma by similar analyses (FIG. 11, middle and lower panels). These results indicate the following possibilities: (1) The inhibition of AP in the plasma may involve secreted factors that may be transported and excreted by these genes ClpV or VgrG and/or corresponding proteins. (2) The factor(s) responsible for the AP inhibitory factor may be bound to the surface of these secretion apparatus Clp V or VgrG.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345;
U.S. Pat. No. 4,275,149
U.S. Pat. No. 4,277,437
U.S. Pat. No. 4,366,241
U.S. Pat. No. 4,376,110
U.S. Pat. No. 4,472,509
U.S. Pat. No. 4,554,101
U.S. Pat. No. 4,676,980

U.S. Pat. No. 4,816,567
U.S. Pat. No. 4,938,948
U.S. Pat. No. 5,021,236
U.S. application. Ser. No. 07/715,272
U.S. application Ser. No. 07/934,373
Adams and Schier, *J. Immunol. Methods*, 231:249-260, 1999.
Atwell et al., *Protein Eng.*, 12:597-604, 1999.
Barker & Klose, *Ann N Y Acad Sci.*, [E-Pub.], March 2007.
Bird et al., *Science*, 242:423-426, 1988.
Brodeur et al., In: *Monoclonal antibody production techniques and applications*, Marcel Dekker, Inc., NY, 51-63, 1987.
Chen et al., *Microb. Pathog.*, 36:311-318, 2004.
Christopher et al., *JAMA*, 278:412-417, 1997.
Clackson et al., *Nature* 352: 624-628, 1991.
Colcher et al., *J. Natl. Cancer Inst.*, 82:1191-1197, 1990.
Colcher et al., *J. Nucl. Med.*, 42:225-241, 1998.
Conlan et al., *Microb. Pathog.*, 34:239-248, 2003.
David et al., *Biochemistry*, 13:1014, 1974.
De Jager et al., *Semin. Nucl. Med.*, 23(2):165-179, 1993.
Dennis et al., *JAMA*, 285:2763-2773, 2001.
Doolittle and Ben-Zeev, *Methods Mol, Biol*, 109:215-237, 1999.
Ellis, *Tularemia. Clin. Microbiol. Rev.*, 15:631-646, 2002.
European Pat. Appln. 03089
Feldman and Feldman, *Nat. Rev. Cancer*, 1:34-45, 2001.
Fernley & Walker, *Biochem. J.* 111:187-194, 1969.
Fortier et al., *Infect. Immun.*, 59:2922-2928, 1991.
Freifelder, In: *Physical Biochemistry Applications to Biochemistry and Molecular Biology*, $2^{nd}$ Ed., 238-246, Wm. Freeman and Co., NY, 1982.
Goding, In: *Monoclonal Antibodies: Principles and Practice*, 2d ed., Academic Press, Orlando, Fla., pp 60-61, 71-74, 1986.
Griffith et al., *EMBO J.*, 12:725-734, 1993.
Gulbis and Galand, *Hum. Pathol.*, 24(12):1271-1285, 1993.
Harris, *Ann. N.Y. Acad. Sci.*, 666:21-52, 1992.
Hunter et al., *Nature*, 144:945, 1962.
Huston et al., *Biochemistry*, 27(25):8945-8952, 1988.
Jakobovits et al., *Nature*, 362:255-258, 1993.
Jakobovits et al., *Proc. Natl. Acad. Sci. USA*, 90:2551-255, 1993.
Johnson et al., In: *Biotechnology and Pharmacy*, Pezzuto et al., eds., Chapman and Hall, New York, 1993.
Jones et al., *Nature*, 321:522-525, 1986.
Katz et al., *Infect. Immun.*, 74:2809-2816, 2006.
Kohler and Milstein, *Nature*, 256:495-497, 1975.
Kozbor, *J. Immunol.*, 133(6):3001-3005, 1984.
Kuroki et al., *Anticancer Res.*, 20(6A):4067-4071 2000.
Lauriano et al., *Proc. Natl. Acad. Sci. U.S.A.*, 101:4246-4249, 2004.
Lauriano et al., *Proc. Natl. Acad. Sci. USA*, 101:4246-4249, 2004.
Lawlor et al., *Mol. Microbiol.*, 58:1054-1073, 2005.
Malik et al., *Infect. Immun.*, 74:3657-3662, 2006.
Marks et al., *Bio/Technol.*, 10:779-783, 1992.
Marks et al., *J. Mol. Biol.* 222: 581-597, 1991.
McCafferty et al., *Nature*, 348:552-553, 1990.
Millstein and Cuello, *Nature*, 305:537-539, 1983.
Nakamura et al., In: *Handbook of Experimental Immunology* ($4^{th}$ Ed.), Weir et al. (Eds), 1:27, Blackwell Scientific Publ., Oxford, 1987.
Nygren, *J. Histochem. Cytochem.*, 30(5):407-412, 1982.
Pain et al., *J. Immunol. Meth.*, 40:219, 1981.
Pammit et al., *Antimicrob. Agents Chemother.* 48:4513-4519, 2004.
Pammit et al., *Infect. Immun.*, 74:2063-2071, 2006.
PCT Appln. WO 91/00360
PCT Appln. WO 92/200373
PCT Appln. WO 93/06213
PCT Appln. WO 93/08829
Riechmann et al., *Nature*, 332(6162):323-327, 1988.
Sambrook et al., In: *Molecular cloning. a laboratory manual*, $2^{nd}$ Ed., Cold Spring Harbor Laboratory Press, Cold Spring Harbor, N.Y., 1989.
Saslaw et al., *Arch. Intern Med.*, 107:134-146. 1961.
Sjostedt, *Curr. Opin. Microbiol.*, 6:66-71, 2003.
Suresh et al., *Methods in Enzymology*, 121:210-228, 1986.
Tarnvik, *Rev. Infect. Dis.*, 11:440-451, 1989.
Traunecker et al., *EMBO*, 10:3655-3659, 1991.
Verhoeyen et al., *Science*, 239(4847):1534-1536, 1988.
Voller et al., *Bull. World Health Organ.*, 53:55-65, 1976.
Waterhouse et al., *Nucl. Acids Res.*, 21:2265-2266, 1993.
Winthrop et al., *Clin. Cancer Res.*, 9:3845s-3853s, 2003.
Zhang et al., *Microb. Pathog.*, 26:121-130, 1999.
Zola, In: *Monoclonal Antibodies. A Manual of Techniques*, CRC Press, Inc., pp. 147-158, 1987.

The invention claimed is:

1. A method for determining whether a subject has a *Francisella* infection comprising detecting alkaline phosphatase (AP) degradation activity in a sample from the subject by detecting degradation of a substrate added to the sample, wherein AP degradation activity is indicative of *Francisella* infection.

2. The method of claim 1, wherein the subject is human.

3. The method of claim 1, wherein the subject is living.

4. The method of claim 1, wherein the sample comprises lung cells, liver cells, blood serum, blood plasma or saliva.

5. The method of claim 4, wherein the sample is a blood serum or plasma sample.

6. The method of claim 1, wherein the substrate is a purified or recombinant AP polypeptide.

7. The method of claim 6, wherein the substrate is a recombinant AP.

8. The method of claim 6, wherein the substrate is labeled.

9. The method of claim 8, wherein the label is fluorescent, colorimetric, enzymatic, or radioactive.

10. The method of claim 8, wherein the substrate is labeled with a fluorophore and a quenching agent and the fluorophore and the quenching agent labels are separated by a polypeptide sequence that is degraded.

11. The method of claim 10, wherein substrate degradation is detected by a change in fluorescence.

12. The method of claim 6, wherein the substrate is immobilized.

13. The method of claim 6, wherein the substrate is a mammalian AP polypeptide.

14. The method of claim 13, wherein the substrate is a human AP polypeptide.

15. The method of claim 1, wherein the substrate is an active AP enzyme.

16. The method of claim 15, wherein the degradation of the added substrate is detected by detecting a loss in AP activity from the added substrate.

17. The method of claim 15, wherein the active AP enzyme is a purified or recombinant mammalian AP.

18. The method of claim 17, wherein the active AP enzyme is calf-intestinal alkaline phosphatase (CIP).

19. The method of claim 1, wherein the subject has been exposed to *Francisella* bacteria.

20. The method of claim 19, wherein the sample is obtained about 8 to about 72 hours after said exposure to *Francisella* bacteria.

21. The method of claim 20, wherein the sample is obtained about 12 to about 72 hours after said exposure to *Francisella* bacteria.

22. The method of claim 21, wherein the sample is obtained about 24 to about 48 hours after said exposure to *Francisella* bacteria.

23. The method of claim 1, further comprising detecting alanine aminotransferase (ALT) activity and aspartate aminotransferase (AST) activity in the sample from the subject; and determining that the subject has a *Francisella* infection if AP degradation activity, ALT activity, and AST activity are increased.

24. A method for determining whether a subject has a *Francisella* infection comprising detecting alkaline phosphatase (AP) degradation activity in a sample from the subject by detecting an AP degradation product in the sample, wherein AP degradation activity is indicative of *Francisella* infection.

25. The method of claim 24, wherein the AP degradation product is detected by antibody binding.

26. The method of claim 25, wherein the AP degradation product is detected by ELISA or Western blot.

27. The method of claim 24, wherein the subject has been exposed to *Francisella* bacteria.

28. The method of claim 27, wherein the sample is obtained about 8 to about 72 hours after said exposure to *Francisella* bacteria.

29. The method of claim 28, wherein the sample is obtained about 12 to about 72 hours after said exposure to *Francisella* bacteria.

30. The method of claim 29, wherein the sample is obtained about 24 to about 48 hours after said exposure to *Francisella* bacteria.

31. The method of claim 24, wherein the subject is human.

32. The method of claim 24, wherein the subject is living.

33. The method of claim 24, wherein the sample comprises lung cells, liver cells, blood serum, blood plasma or saliva.

34. The method of claim 33, wherein the sample is a blood serum or plasma sample.

35. The method of claim 24, further comprising detecting alanine aminotransferase (ALT) activity and aspartate aminotransferase (AST) activity in the sample from the subject; and determining that the subject has a *Francisella* infection if AP degradation activity, ALT activity, and AST activity are increased.

36. A method for assisting in determining whether a subject has a *Francisella* infection, comprising:
   a) detecting AP degradation activity in a sample from the subject; and
   b) reporting information regarding AP degradation activity in the sample.

37. A method for treating an infection in a subject comprising:
   a) obtaining or having a sample from a subject;
   b) detecting AP degradation activity in the sample, wherein AP degradation activity is indicative *Francisella* infection; and
   c) treating the subject with an antibiotic that is effective against *Francisella* infection or another drug depending on whether AP degradation activity is detected.

38. A method for determining the presence of *Francisella* bacteria in a sample comprising detecting AP degradation activity in the sample by detecting degradation of a substrate added to the sample.

39. The method of claim 38, wherein the sample is a food, water, air or biological sample.

40. The method of claim 39, wherein the biological sample is tissue or blood sample.

41. The method of claim 40, wherein the blood sample is a blood serum sample.

42. The method of claim 38, wherein the substrate is a purified or recombinant AP polypeptide.

43. The method of claim 42, wherein the substrate is immobilized.

44. The method of claim 42, wherein the substrate is a mammalian AP polypeptide.

45. The method of claim 44, wherein the substrate is a human AP polypeptide.

46. The method of claim 38, wherein the substrate added to the sample is an active AP enzyme.

47. The method of claim 46, wherein the degradation of added substrate is detected by detecting a loss in AP activity from the added substrate.

48. The method of claim 46, wherein the active AP enzyme is a purified or recombinant mammalian AP.

49. The method of claim 48, wherein the active AP enzyme is calf-intestinal alkaline phosphatase (CIP).

50. The method of claim 42, wherein the substrate is a recombinant AP.

51. The method of claim 42, wherein the substrate is labeled.

52. The method of claim 51, wherein the label is fluorescent, colorimetric, enzymatic, or radioactive.

53. The method of claim 51, wherein the substrate is labeled with a fluorophore and a quenching agent and the fluorophore and the quenching agent labels are separated by a polypeptide sequence that is degraded.

54. The method of claim 53, wherein substrate degradation is detected by a change in fluorescence.

55. A method for determining the presence of *Francisella* bacteria in a sample comprising detecting AP degradation activity in the sample by detecting an AP degradation product in the sample.

56. The method of claim 55, wherein the AP degradation product is detected by antibody binding.

57. The method of claim 56, wherein the AP degradation product is detected by ELISA or Western blot.

58. The method of claim 55, wherein the sample is a food, water, air or biological sample.

59. The method of claim 58, wherein the biological sample is tissue or blood sample.

60. The method of claim 59, wherein the blood sample is a blood serum sample.

61. A method for determining the efficacy of a *Francisella* vaccine composition in a subject comprising:
   a) administering a *Francisella* vaccine composition to a subject;
   b) administering a *Francisella* bacteria to the subject wherein the *Francisella* bacteria is capable of reducing AP activity in the serum of an unvaccinated subject;
   c) obtaining a sample from the subject; and
   d) determining the amount of AP degradation activity in the sample, thereby determining the efficacy of the vaccine composition.

62. The method of claim 61, further defined as a method for determining an effective amount of a *Francisella* vaccine composition.

63. The method of claim 61, wherein the *Francisella* vaccine composition is administered two or more times prior to administration of said *Francisella* bacteria.

64. The method of claim 61, wherein the subject is a laboratory animal.

65. The method of claim 61, wherein said *Francisella* bacteria is a pathogenic *Francisella* bacteria.

66. The method of claim 61, wherein determining the amount of AP degradation activity in the sample is by determining the AP activity in a blood sample.

67. The method of claim 66, wherein determining AP degradation activity in a blood sample comprises measuring a reduction in serum AP activity after administration of said *Francisella* bacteria.

68. The method of claim 61, further defined as a method for comparing the efficacy of two or more vaccine compositions comprising:

a) administering each *Francisella* vaccine composition to a separate subject;
b) administering a *Francisella* bacteria to each subject wherein the *Francisella* bacteria is capable of reducing AP activity in the serum of an unvaccinated subject;
c) obtaining a sample from each of the subjects; and
d) determining the amount of AP degradation activity in the samples, thereby determining the relative efficacy of the vaccine compositions.

* * * * *

UNITED STATES PATENT AND TRADEMARK OFFICE
CERTIFICATE OF CORRECTION

PATENT NO. : 8,076,099 B2  
APPLICATION NO. : 12/133963  
DATED : December 13, 2011  
INVENTOR(S) : James Chambers et al.

Page 1 of 1

It is certified that error appears in the above-identified patent and that said Letters Patent is hereby corrected as shown below:

In column 1, lines 9-11, delete paragraph and insert
--This invention was made with government support under grant number O1 AI057986 awarded by the National Institutes of Health. The government has certain rights in the invention.-- therefor.

Signed and Sealed this
Sixth Day of March, 2012

David J. Kappos
*Director of the United States Patent and Trademark Office*